United States Patent
Galdonik et al.

(10) Patent No.: US 9,662,129 B2
(45) Date of Patent: May 30, 2017

(54) ASPIRATION CATHETERS FOR THROMBUS REMOVAL

(75) Inventors: Jason A. Galdonik, Hanover, MN (US); Edward Anderson, Maple Grove, MN (US); Kavitha Ganesan, Maple Grove, MN (US); Greg Boldenow, St. Michael, MN (US); John Kirchgessner, St. Louis Park, MN (US); Grazyna Wlodarski, Andover, MN (US)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 13/467,798

(22) Filed: May 9, 2012

(65) Prior Publication Data
US 2012/0253313 A1 Oct. 4, 2012

Related U.S. Application Data

(60) Continuation of application No. 13/117,452, filed on May 27, 2011, which is a division of application No.
(Continued)

(51) Int. Cl.
*A61M 31/00* (2006.01)
*A61B 17/22* (2006.01)
(Continued)

(52) U.S. Cl.
CPC ............ *A61B 17/22* (2013.01); *A61B 17/221* (2013.01); *A61B 17/2909* (2013.01);
(Continued)

(58) Field of Classification Search
CPC .......... A61M 25/0045; A61M 25/0009; A61M 2025/0034; A61M 2025/0042; A61M 25/0012
(Continued)

(56) References Cited

U.S. PATENT DOCUMENTS 2,730,101 A 1/1956 Hoffman
3,949,757 A 4/1976 Sabel
(Continued)

FOREIGN PATENT DOCUMENTS

EP 0117940 A2 9/1984
EP 1226795 A2 7/2002
(Continued)

OTHER PUBLICATIONS

Feldman, "Transcatheter Aspiration of a Thrombus in an Aortocoronary Saphenous Vein Graft," Am J Cardiol 1987, 60(4):379-380.
(Continued)

*Primary Examiner* — Phillip Gray
(74) *Attorney, Agent, or Firm* — Christensen, Fonder, Dardi & Herbert PLLC; Peter S. Dardi

(57) ABSTRACT

Systems for less invasive medical procedures comprise a filter device mounted on an integrated guiding structure and an aspiration catheter. These components can be used together or separately, and the system can be used with other medical devices that are designed for less invasive procedures, such as procedures in a patient's vasculature. The catheter can have a radiopaque band that is held in place under metal wire embedded within the polymer forming the tube of the catheter. In some embodiments, the aspiration catheter has a small diameter distal portion that can access into small diameter vessels in which the distal portion has a smaller average diameter than the remaining tube of the catheter.

17 Claims, 23 Drawing Sheets

Related U.S. Application Data

12/218,306, filed on Jul. 14, 2008, now Pat. No. 8,070,694.

(51) Int. Cl.
  A61B 17/221 (2006.01)
  A61B 17/29 (2006.01)
  A61M 25/01 (2006.01)
  A61B 17/28 (2006.01)
  A61B 17/00 (2006.01)
  A61F 2/01 (2006.01)
  A61M 25/00 (2006.01)

(52) U.S. Cl.
  CPC ..... *A61M 25/0108* (2013.01); *A61B 17/2833* (2013.01); *A61B 2017/0046* (2013.01); *A61B 2017/22079* (2013.01); *A61B 2017/292* (2013.01); *A61B 2017/2923* (2013.01); *A61F 2/013* (2013.01); *A61M 2025/0008* (2013.01)

(58) Field of Classification Search
  USPC ... 604/500–532, 96.01, 164.01, 95.01–95.05
  See application file for complete search history.

(56) References Cited

U.S. PATENT DOCUMENTS

| | | |
|---|---|---|
| 3,996,938 A | 12/1976 | Clark, III |
| 4,020,829 A | 5/1977 | Willson et al. |
| 4,033,331 A | 7/1977 | Guss et al. |
| 4,174,715 A | 11/1979 | Hasson |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engelson |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,883,460 A | 11/1989 | Zanetti |
| 4,887,613 A | 12/1989 | Farr et al. |
| 4,900,303 A | 2/1990 | Lemelson |
| 4,921,484 A | 5/1990 | Hillstead |
| 4,994,067 A | 2/1991 | Summers |
| 4,998,919 A * | 3/1991 | Schnepp-Pesch et al. .......... 604/164.09 |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,161,534 A | 11/1992 | Berthiaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,211,651 A | 5/1993 | Reger et al. |
| 5,219,332 A | 6/1993 | Nelson et al. |
| 5,308,318 A | 5/1994 | Plassche, Jr. |
| 5,312,338 A | 5/1994 | Nelson et al. |
| 5,325,868 A | 7/1994 | Kimmelstiel |
| 5,352,197 A | 10/1994 | Hammersmark et al. |
| 5,392,778 A | 2/1995 | Horzewski |
| 5,395,383 A | 3/1995 | Adams et al. |
| 5,423,331 A | 6/1995 | Wysham |
| 5,438,993 A | 8/1995 | Lynch et al. |
| 5,465,716 A | 11/1995 | Avitall |
| 5,485,667 A | 1/1996 | Kleshinski |
| 5,490,859 A | 2/1996 | Mische et al. |
| 5,501,694 A | 3/1996 | Ressemann et al. |
| 5,527,292 A | 6/1996 | Adams et al. |
| 5,533,967 A | 7/1996 | Imran |
| 5,546,958 A | 8/1996 | Thorud et al. |
| 5,549,626 A | 8/1996 | Miller et al. |
| 5,571,122 A | 11/1996 | Kelly et al. |
| 5,578,009 A | 11/1996 | Kraus et al. |
| 5,599,307 A | 2/1997 | Bacher et al. |
| 5,720,764 A | 2/1998 | Naderlinger |
| 5,766,191 A | 6/1998 | Trerotola |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,836,868 A | 11/1998 | Ressemann et al. |
| 5,843,002 A | 12/1998 | Pecor et al. |
| 5,843,051 A | 12/1998 | Adams et al. |
| 5,851,189 A | 12/1998 | Forber |
| 5,882,329 A | 3/1999 | Patterson et al. |
| 5,897,567 A | 4/1999 | Ressemann et al. |
| 5,899,890 A | 5/1999 | Chiang et al. |
| 5,910,154 A | 6/1999 | Tsugita et al. |
| 5,911,725 A | 6/1999 | Boury |
| 5,911,734 A | 6/1999 | Tsugita et al. |
| 5,928,260 A | 7/1999 | Chin et al. |
| 5,935,139 A | 8/1999 | Bates |
| 5,938,645 A | 8/1999 | Gordon |
| 5,941,869 A | 8/1999 | Patterson et al. |
| 5,972,019 A | 10/1999 | Engelson et al. |
| 5,997,557 A | 12/1999 | Barbut et al. |
| 6,010,522 A | 1/2000 | Barbut et al. |
| 6,022,336 A | 2/2000 | Zadno-Azizi et al. |
| 6,030,349 A | 2/2000 | Wilson et al. |
| 6,030,369 A * | 2/2000 | Engelson .......... A61M 25/0045 604/264 |
| 6,066,149 A | 5/2000 | Samson et al. |
| 6,117,141 A | 9/2000 | Ouchi |
| 6,135,991 A | 10/2000 | Muni et al. |
| 6,142,987 A | 11/2000 | Tsugita |
| 6,146,396 A | 11/2000 | Konya et al. |
| 6,159,195 A | 12/2000 | Ha et al. |
| 6,168,579 B1 | 1/2001 | Tsugita |
| 6,203,561 B1 | 3/2001 | Ramee et al. |
| 6,206,868 B1 | 3/2001 | Parodi |
| 6,221,049 B1 * | 4/2001 | Selmon et al. .......... 604/164.13 |
| 6,238,402 B1 | 5/2001 | Sullivan, III et al. |
| 6,238,412 B1 | 5/2001 | Dubrul et al. |
| 6,240,231 B1 | 5/2001 | Ferrera et al. |
| 6,258,115 B1 | 7/2001 | Dubrul |
| 6,270,477 B1 | 8/2001 | Bagaoisan et al. |
| 6,277,139 B1 | 8/2001 | Levinson et al. |
| 6,306,163 B1 | 10/2001 | Fitz |
| 6,346,116 B1 | 2/2002 | Brooks et al. |
| 6,361,545 B1 | 3/2002 | Macoviak et al. |
| 6,368,338 B1 | 4/2002 | Konya et al. |
| 6,391,044 B1 | 5/2002 | Yadav et al. |
| 6,454,741 B1 | 9/2002 | Muni et al. |
| 6,454,775 B1 | 9/2002 | Demarais et al. |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,537,295 B2 | 3/2003 | Petersen |
| 6,540,768 B1 | 4/2003 | Diaz et al. |
| 6,551,302 B1 | 4/2003 | Rosinko et al. |
| 6,558,405 B1 | 5/2003 | McInnes |
| 6,569,148 B2 | 5/2003 | Bagaoisan et al. |
| 6,579,484 B1 * | 6/2003 | Tiernan .......... A61M 25/0009 264/173.16 |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |
| 6,620,148 B1 | 9/2003 | Tsugita |

(56) References Cited

U.S. PATENT DOCUMENTS

| | | | |
|---|---|---|---|
| 6,695,865 | B2 | 2/2004 | Boyle et al. |
| 6,702,834 | B1 | 3/2004 | Boylan et al. |
| 6,773,448 | B2 | 8/2004 | Kusleika et al. |
| 6,805,684 | B2 | 10/2004 | Bonnette et al. |
| 6,805,692 | B2 | 10/2004 | Muni et al. |
| 6,866,669 | B2 | 3/2005 | Buzzard et al. |
| 6,878,151 | B2 | 4/2005 | Carrison et al. |
| 6,879,854 | B2 | 4/2005 | Windheuser et al. |
| 6,911,036 | B2 | 6/2005 | Douk et al. |
| 6,945,956 | B2 | 9/2005 | Waldhauser et al. |
| 6,949,104 | B2 | 9/2005 | Griffis et al. |
| 6,951,570 | B2 | 10/2005 | Linder et al. |
| 6,958,059 | B2 | 10/2005 | Zadno-Azizi |
| 6,969,395 | B2 | 11/2005 | Eskuri |
| 6,991,642 | B2 | 1/2006 | Petersen |
| 7,052,500 | B2 | 5/2006 | Bashiri et al. |
| 7,056,328 | B2 | 6/2006 | Arnott |
| 7,115,134 | B2 | 10/2006 | Chambers |
| 7,115,138 | B2 | 10/2006 | Renati et al. |
| 7,166,120 | B2 | 1/2007 | Kusleika |
| 7,220,271 | B2 | 5/2007 | Clubb et al. |
| 7,229,431 | B2 | 6/2007 | Houser et al. |
| 7,229,463 | B2 | 6/2007 | Sutton et al. |
| 7,229,464 | B2 | 6/2007 | Hanson et al. |
| 7,232,452 | B2 | 6/2007 | Adams et al. |
| 7,309,334 | B2 | 12/2007 | von Hoffmann |
| 7,549,974 | B2 | 6/2009 | Nayak |
| 7,736,355 | B2 | 6/2010 | Itou et al. |
| 7,842,055 | B2 * | 11/2010 | Pintor et al. ............... 606/159 |
| 7,938,820 | B2 | 5/2011 | Webster et al. |
| 8,021,351 | B2 | 9/2011 | Boldenow et al. |
| 8,048,032 | B2 | 11/2011 | Root et al. |
| 8,231,600 | B2 | 7/2012 | von Hoffmann |
| 8,308,712 | B2 | 11/2012 | Provost et al. |
| 2001/0044632 | A1 | 11/2001 | Daniel et al. |
| 2001/0051811 | A1 | 12/2001 | Bonnette et al. |
| 2002/0035347 | A1 | 3/2002 | Bagaoisan et al. |
| 2002/0055747 | A1 | 5/2002 | Cano et al. |
| 2002/0062133 | A1 | 5/2002 | Gilson et al. |
| 2002/0095174 | A1 | 7/2002 | Tsugita et al. |
| 2002/0111648 | A1 | 8/2002 | Kusleika et al. |
| 2002/0133111 | A1 | 9/2002 | Shadduck |
| 2002/0143362 | A1 | 10/2002 | Macoviak et al. |
| 2002/0151927 | A1 | 10/2002 | Douk et al. |
| 2002/0165574 | A1 | 11/2002 | Ressemann et al. |
| 2002/0169472 | A1 | 11/2002 | Douk et al. |
| 2002/0183782 | A1 | 12/2002 | Tsugita et al. |
| 2003/0023263 | A1 | 1/2003 | Krolik et al. |
| 2003/0065353 | A1 | 4/2003 | Horzewski et al. |
| 2003/0120208 | A1 | 6/2003 | Houser et al. |
| 2003/0135232 | A1 | 7/2003 | Douk et al. |
| 2004/0006344 | A1 | 1/2004 | Nguyen et al. |
| 2004/0006365 | A1 | 1/2004 | Brady et al. |
| 2004/0015151 | A1 | 1/2004 | Chambers |
| 2004/0153118 | A1 | 8/2004 | Clubb et al. |
| 2004/0220611 | A1 | 11/2004 | Ogle |
| 2004/0254602 | A1 | 12/2004 | Lehe et al. |
| 2005/0021075 | A1 | 1/2005 | Bonnette et al. |
| 2005/0021152 | A1 | 1/2005 | Ogle et al. |
| 2005/0085847 | A1 | 4/2005 | Galdonik et al. |
| 2005/0209631 | A1 | 9/2005 | Galdonik et al. |
| 2005/0228479 | A1 | 10/2005 | Pavcnik et al. |
| 2005/0277976 | A1 | 12/2005 | Galdonik et al. |
| 2006/0030876 | A1 | 2/2006 | Peacock, III et al. |
| 2006/0047301 | A1 | 3/2006 | Ogle |
| 2006/0129091 | A1 | 6/2006 | Bonnette et al. |
| 2006/0200047 | A1 | 9/2006 | Galdonik et al. |
| 2006/0200191 | A1 | 9/2006 | Zadno-Azizi |
| 2007/0060908 | A1 | 3/2007 | Webster et al. |
| 2007/0060911 | A1 | 3/2007 | Webster et al. |
| 2007/0060944 | A1 | 3/2007 | Boldenow et al. |
| 2007/0135733 | A1 | 6/2007 | Soukup et al. |
| 2007/0250040 | A1 * | 10/2007 | Provost ............. A61M 25/0012 604/525 |
| 2007/0250096 | A1 | 10/2007 | Yamane et al. |
| 2007/0260115 | A1 | 11/2007 | Brock et al. |
| 2008/0086110 | A1 | 4/2008 | Galdonik et al. |
| 2008/0109088 | A1 | 5/2008 | Galdonik et al. |
| 2008/0172066 | A9 | 7/2008 | Galdonik et al. |
| 2010/0204672 | A1 | 8/2010 | Lockhart et al. |

FOREIGN PATENT DOCUMENTS

| | | | |
|---|---|---|---|
| GB | 2020557 | A | 11/1979 |
| WO | 95/05209 | A1 | 2/1995 |
| WO | 98/38930 | A1 | 9/1998 |
| WO | 00/16705 | A1 | 3/2000 |
| WO | 02/055146 | A1 | 7/2002 |
| WO | 02/085092 | A2 | 10/2002 |

OTHER PUBLICATIONS

Mak et al., "Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications." Am J Cardiol 1997, 80(8):985-988. (Abstract).

Mathew et al., "The Influence of Abciximab Use on Clinical Outcome After Aortocoronary Vein Graft Interventions," J Am Coll Cardiol 1999, 34(4):1163-1169.

Nakagawa et al, "A Retrievable Nitinol Vena Cava Filter: Experimental and Initial Clinical Results," J of Vascular and Interventional Radiology, 1994, 5:507-512.

Webb et al., "Retrieval and Analysis of Particulate Debris After Saphenous Vein Graft Intervention," J Am Coll Cardiol 1999, 34(2);468-475.

4DG Fibers: http://web.archive.org/web/20011030070010/http://fitfibers.com/4DG_Fibers.htm; (Oct. 30, 2001).

Fiber Innovative Technology: biocomponent and specialty fibers; FIT Capabilities; http://web.archive.org/web/20010217040848/http://www.fitfibers.com/capabilities.htm (Feb. 17, 2001).

Fiber Innovative Technology: biocomponent and specialty fibers; FIT Capabilities; http://web.archive.org/web/20010408003529/http://www.fitfibers.com/product.htm.

Office Action for prior U.S. Appl. No. 13/117,452, mailed Dec. 13, 2012.

Response to Office Action for co-pending U.S. Appl. No. 13/117,452, dated Mar. 7, 2013 (10 pages).

Office Action for co-pending U.S. Appl. No. 13/117,452, dated Mar. 26, 2013 (17 pages).

Response to Office Action for co-pending U.S. Appl. No. 13/117,452, dated Apr. 5, 2013 (10 pages).

Advisory Action for co-pending U.S. Appl. No. 13/117,452, dated Apr. 25, 2013 (14 pages).

Reeder et al., "Aspiration Thrombectomy for Removal of Coronary Thrombosis," American Journal of Cardiology (Jul. 1, 1992) 70:107-110 (Abstract only).

Office Action for co-pending U.S. Appl. No. 13/117,452, dated Jul. 26, 2013 (14 pages).

Examiner's Answer for co-pending U.S. Appl. No. 13/117,452, dated May 14, 2014 (9 pages).

Penumbra, Inc., "Penumbra, Inc. Completes Pivotal Stroke Trial of Intracranial Revascularization," Press Release (2007).

Penumbra System: Continuous Aspiration Thrombectomy Marketing brochure © 2010.

Penumbra 5Max Marketing brochure © 2013.

Penumbra, Inc., "The Penumbra Pivotal Stroke Trial: Safety and Effectiveness of a New Generation of Mechanical Devices for Clot Removal in Intracranial Large Vessel Occlusive Disease," Stroke 2009, 40:2761-2768.

Yoo et al., "The Penumbra Stroke System: a technical review," J NeuroIntervent Surg 2012, 4:199-205.

Abstracts from the 2007 International Stroke Conference, 38 Stroke 453-607 (2007).

Response to Office Action for co-pending U.S. Appl. No. 13/117,452 dated Sep. 4, 2013 (9 pages).

(56) References Cited

OTHER PUBLICATIONS

Final Office Action for co-pending U.S. Appl. No. 13/117,452 dated Sep. 27, 2013 (13 pages).
Response After Final for co-pending U.S. Appl. No. 13/117,452 dated Oct. 31, 2013 (12 pages).
Advisory Action for co-pending U.S. Appl. No. 13/117,452 dated Nov. 8, 2013 with listing of Penumbra articles (12 pages).
Supplemental Response for co-pending U.S. Appl. No. 13/117,452 dated Nov. 19, 2013 (9 pages).
Advisory Action for co-pending U.S. Appl. No. 13/117, 452 dated Nov. 27, 2013 (8 pages).
Appeal Brief for co-pending U.S. Appl. No. 13/117,452, dated Jan. 7, 2014.
Office Action for co-pending U.S. Appl. No. 13/117,452, dated Feb. 21, 2014 (7 pages).
Response to Office Action for co-pending U.S. Appl. No. 13/117,452, dated Mar. 11, 2014 (9 pages).
Interview Summary for co-pending U.S. Appl. No. 13/117,452, dated Mar. 13, 2014 (3 pages).
Final Office Action for co-pending U.S. Appl. No. 13/117,452 dated Mar. 20, 2014 (13 pages).
Response After Final for co-pending U.S. Appl. No. 13/117,452 dated Mar. 28, 2014 (13 pages).
Advisory Action for co-pending U.S. Appl. No. 13/117,452 dated Apr. 3, 2014 (6 pages).
Appeal Brief for co-pending U.S. Appl. No. 13/117,452, dated Apr. 16, 2014 (22 pages).
Reply Brief for co-pending U.S. Appl. No. 13/117,452, dated Jun. 4, 2014 (15 pages).

* cited by examiner

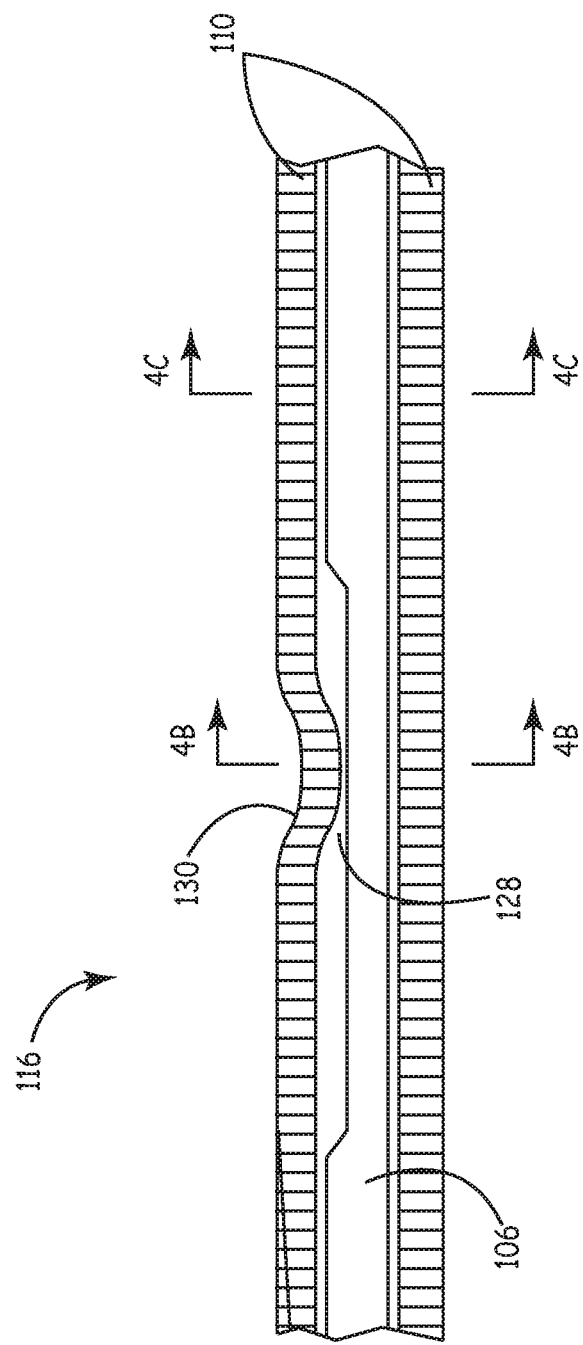

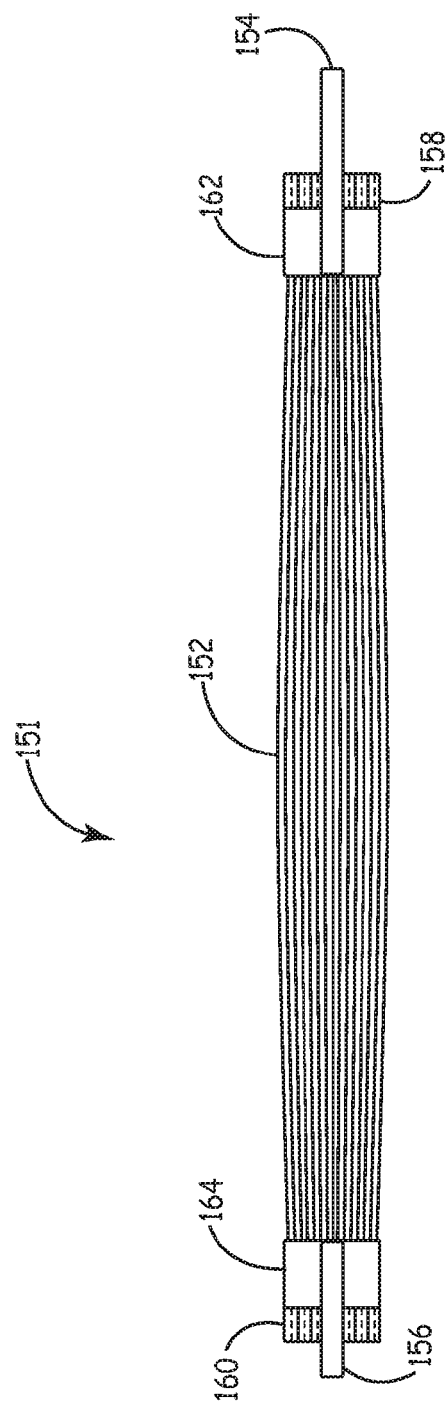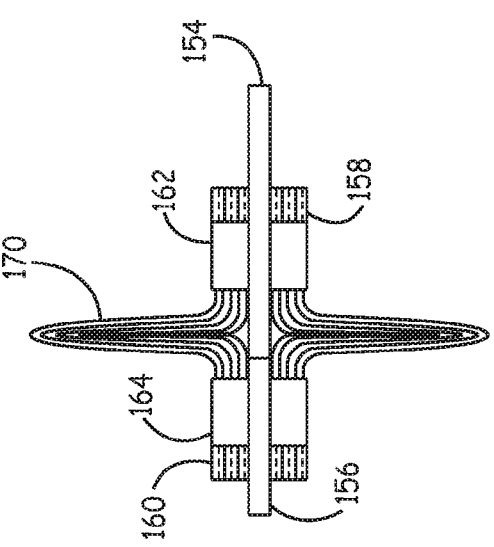

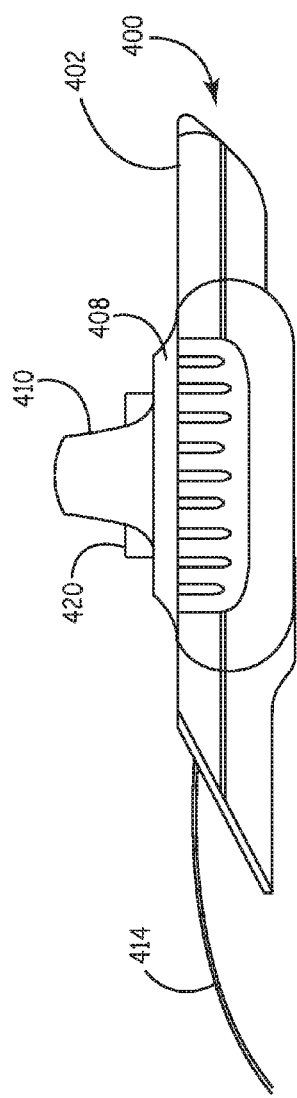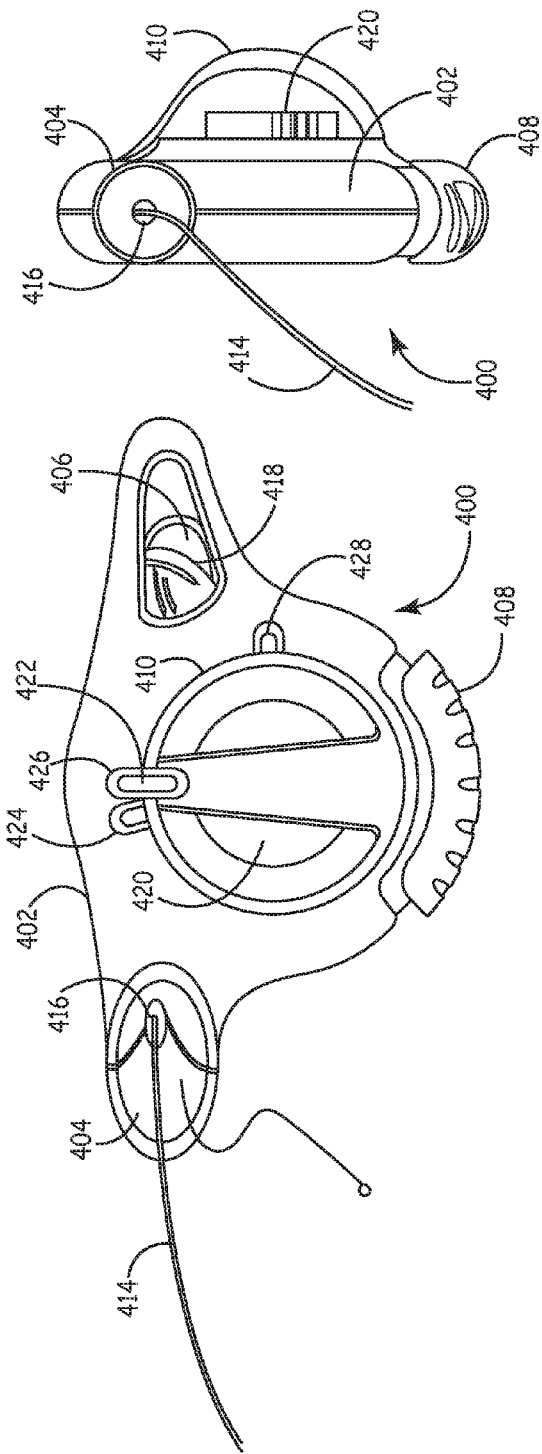

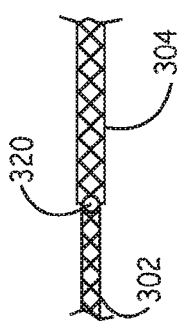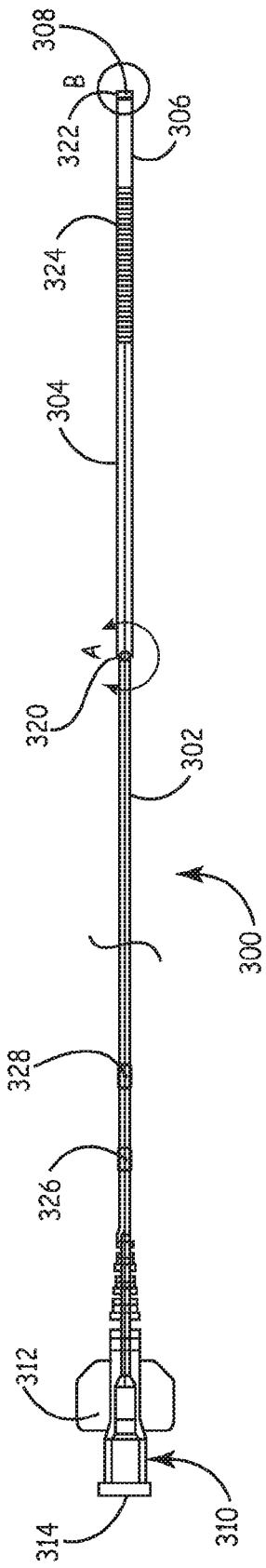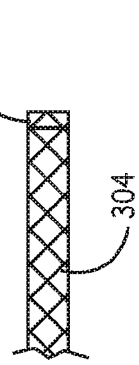
FIG. 18A
FIG. 18
FIG. 18B

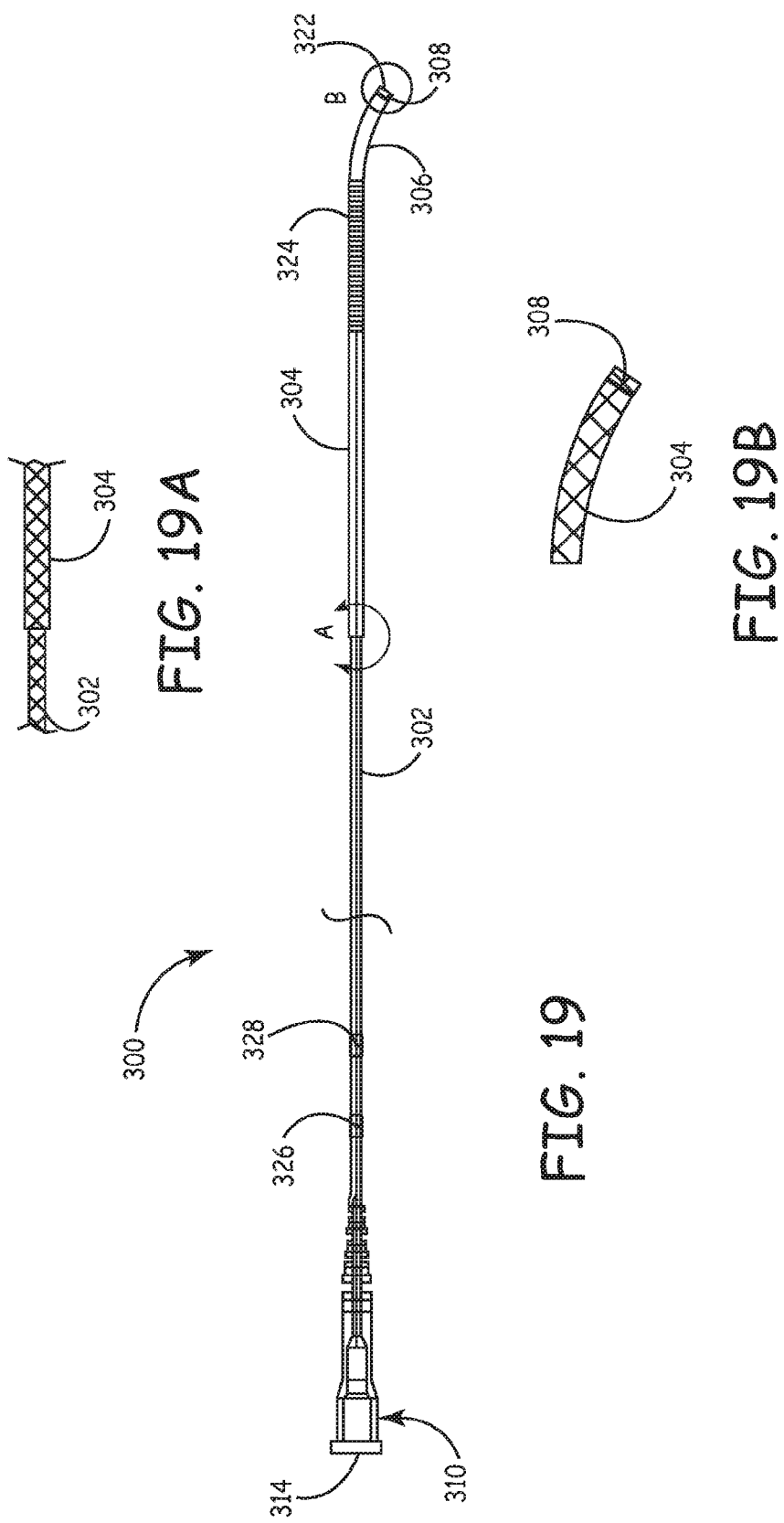

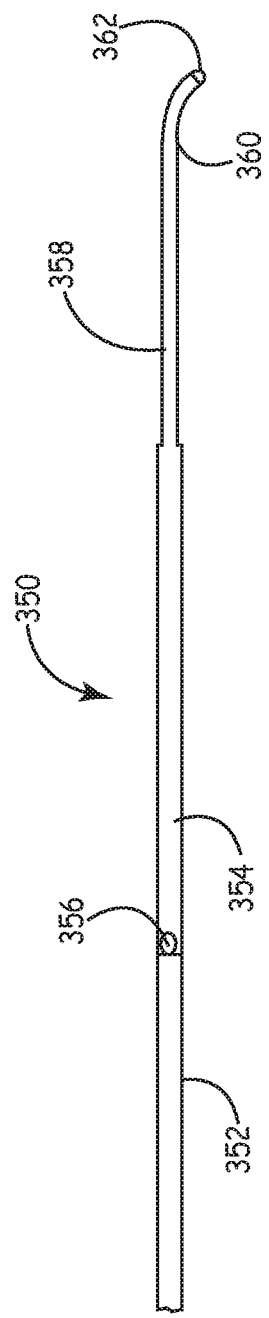

ASPIRATION CATHETERS FOR THROMBUS REMOVAL

CROSS REFERENCE TO RELATED APPLICATIONS

This application is a continuation of U.S. patent application Ser. No. 13/117,452 filed on May 27, 2011 to Galdonik et al., entitled "Aspiration Catheters for Thrombus Removal," which is a divisional of U.S. patent application Ser. No. 12/218,306, now U.S. Pat. No. 8,070,694 filed on Jul. 14, 2008 to Galdonik et al., entitled "Fiber Based Medical Devices and Aspiration Catheters," both incorporated herein by reference.

FIELD OF THE INVENTION

The invention relates to medical devices, such as fiber-based vascular devices, for less invasive medical procedures, such as embolic protection and/or embolectomy procedures. Thus, the devices are able to capture and retrieve thrombus and debris generally from vessels, in which the thrombus or debris is preexisting in the vessel or generated by a procedure in the vessel with the filter device in a deployed configuration. The invention further relates to aspiration catheters that are suitable for retrieving the fiber-based device as well as for performing thrombectomy procedures and the like.

BACKGROUND OF THE INVENTION

A variety of procedures are performed with less invasive approaches to reach distant locations within a patient's body. These procedures can be used, for example, for entry into the abdominal cavity or into the urinary track, or for reaching the patient's genitals. However, many of the procedures are performed within the cardiovascular system. For any of these procedures, a guidewire can be used to snake through the patient to position the tip of the guidewire at a desired location. A catheter and/or other medical devices can be positioned by sliding them over the guidewire to the appropriate location.

Generally, to position the guidewire, the guidewire traverses along a pathway, such as through vessels of the cardiovascular system, that has bends and branches. To navigate along the curves and branches, the guidewires and catheters are flexible. To steer the device to the desired location, some control generally should be possible with respect to directing the tip of the device for steering along curves and branches in the desired pathway. Through the application of torque at the proximal end of the device protruding from the patient, the tip can be guided along a selected path within the patient. The delivery of the device is facilitated through the use of real time imaging.

Many less invasive procedures create the possibility of emboli formation as a result of the procedure. Also, some procedures may be specifically initiated to capture and/or remove emboli, which are generated or have a risk of being generated through another mechanism. An embolus can be any particle comprising a foreign and/or native material, which enters the vascular system or other vessel of the body with potential to cause occlusion of flow, e.g., blood flow. Emboli can be formed from aggregates of fibrin, blood cells or fragments thereof, collagen, cholesterol, plaque, fat, calcified plaque, bubbles, arterial tissue, and/or other miscellaneous fragments or combinations thereof. Emboli can lodge, for example, in the narrowing regions of medium size blood vessels that feed the major organs. Loss of blood flow to surrounding tissue causes localized cell death or micro-infarcts. Cerebral micro-infarcts can cause stroke leading to confusion, disturbance of speech, paralysis, visual disturbances, balance disturbances and even death. In the heart, emboli can cause myocardial infarcts, i.e. heart attacks. Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding micro-infarctions/micro-infarcs. Resulting impairments are frequently short term but can be permanent.

Many clinical procedures can result in emboli including, for example, coronary, carotid, and peripheral interventions. In these cases, particulate matter, including, for example, plaque, debris and thrombus, can form emboli distal to the site of intervention. As a result, blood flow to the distal vascular bed can be diminished and periprocedural end-organ ischemia and infarction can result. Distal embolization of large particles produced at the time of such interventions as balloon inflation or stent deployment may obstruct large, epicardial vessels, and smaller particles (as small as 15-100 microns) can cause micro-infarcts and/or myocardial infarctions and left ventricular dysfunction.

A significant reason for ischemic injury during percutaneous procedures can be generation of emboli that block smaller distal vessels. One approach to curb this complication has been to use pharmacological therapies during the time of the intervention. Limited therapeutic success has been reported with the use of calcium channel blockers, adenosine, and sodium nitroprusside (Webb, J G, Carere, R G, Virmani, R, Baim, D, Teirstein, P S, Whitlow, P, McQueen, C, Kolodgie, F D, Buller, E, Dodek, A, Mancini, G B, & Oesterle, S: Retrieval and analysis of particulate debris after saphenous vein graft intervention. *J Am Coll Cardiol* 2000, 34:468-475, incorporation herein by reference.). Glyoprotein IIb/IIIa inhibitors have been used for percutaneous coronary interventions to reduce platelet aggregation, but also fail to show meaningful long term clinical benefit. (Mathew, V, Grill, D E, Scott, C G, Grantham, J A, Ting, H H, Garratt, K N, & Holmes, D R, Jr. The influence of abciximab use on clinical outcome after aortocoronary vein graft interventions. *J Am Coll Cardiol* 1999, 34:1163-1169 and Mak, K H, Challapalli, R, Eisenberg, M J, Anderson, K M, Califf, R M, & Topol, E J: Effect of platelet glycoprotein IIb/IIIa receptor inhibition on distal embolization during percutaneous revascularization of aortocoronary saphenous vein grafts. EPIC Investigators. Evaluation of IIb/IIIa platelet receptor antagonist 7E3 in Preventing Ischemic Complications. *Am J Cardiol* 1997, 80:985-988, both of which are incorporated herein by reference.) Since embolization often develops from physical disruption of fibrotic plaque, a mechanism of therapeutic embolic protection specifically targeted at prevention of platelet aggregation and blood clotting may have little effect on these already-formed, embolizable plaques.

SUMMARY OF THE INVENTION

In a first aspect, the invention pertains to an actuation tool for manipulating a medical device comprising an overtube and a corewire within a lumen of the overtube, wherein a proximal end of the corewire extends from a proximal end of the overtube. The actuation tool comprises a support structure, an overtube connection supported by the support structure, a corewire connection supported by the support structure, an adjustable channel and a control element comprising a rotatable element, such as a knob, and a lateral transmission operably connected to the adjustable channel. The overtube connection comprises a fastening element configured for gripping the overtube at or near its proximal end with the corewire extending outward from the overtube. The corewire connection generally comprises a corewire connecting element configured to grip the corewire at or near its proximal end. The adjustable channel can comprise slidably engaging elements forming a lumen between the engaging elements. The adjustable channel is supported within the body with the adjustable channel extending between the tube connection and the corewire connection. The lumen of the adjustable channel has a diameter larger than the diameter of the corewire. The lateral movement of the engaging elements changes the relative distance of the overtube connection and the corewire connection. The transmission of the control element converts rotational motion of the rotatable element to relative translational motion of the engaging elements to adjust the relative distance of the overtube connection and the corewire connection to move the proximal ends of the tube and the corewire toward or away from each other when the overtube and corewire are respectively gripped by the corewire connection and the overtube connection.

In further embodiments, the invention pertains to a fiber-based device comprising an overtube, a corewire and a fiber cartridge. The overtube comprising a proximal end, a distal end, and a lumen extending therethrough. The corewire comprises a proximal end and a distal end, and the corewire extends through the lumen of the overtube. The fiber cartridge comprises a bundle of flexible fibers, a first radiopaque marker and a second radiopaque marker. The first radiopaque marker is associated directly or indirectly with a first end of the bundle of fibers. The second radiopaque marker is associated directly or indirectly with a second end of the bundle of fibers, and the fiber cartridge has a deployed configuration having the first marker band and the second marker band projecting a single merged image. In some embodiments, the first radiopaque marker comprises a first tube, and the second radiopaque marker comprises a second tube, each tube having a lumen through the center of the tubes. The bundle of fibers can comprise flexible polymer fibers.

In other aspects, the invention pertains to a medical device comprising an overtube, a corewire, a resilient segment and a torque coupler. The overtube comprises a proximal end, a distal end, and a lumen extending therethrough. Also, the corewire comprises a proximal end and a distal end, and the corewire extends through the lumen of the overtube with the proximal end of the corewire extending from the proximal end of the overtube and the distal end of the corewire extending from the distal end of the overtube. The resilient segment generally directly or indirectly attaches to the distal end of the tub. Furthermore, the torque coupler comprising a corewire coupling element integral with the corewire and a resilient segment coupling element integral with the resilient segment in which the corewire coupling element engages with the resilient segment coupling element to couple the rotational motion of the resilient segment with the corewire.

In additional aspects, the invention pertains to a catheter comprising a tube, a radiopaque band and metal wire. The tube comprises a polymer, and the tube has a proximal portion and a distal portion. The radiopaque band generally is in contact with the distal portion of the tube. The metal wire generally has at least a portion of which embedded in the polymer and is extending over the radiopaque band.

Furthermore, the invention pertains to an aspiration catheter comprising a connector, a proximal portion, a distal tip and a tube connected between the distal tip and the proximal portion. The connector generally is attached to the proximal portion to provide a passageway to the distal tip through a continuous lumen extending from the proximal portion to the distal tip. In some embodiments, the distal tip has an average outer diameter from about 25 percent to about 90 percent of the average outer diameter of the tube.

Moreover, the invention pertains to a method for loading a medical device into an actuation tool. The medical device comprises an overtube and a corewire within a lumen of the tube with a proximal end of the corewire extending from a proximal end of the tube. The actuation tool comprises an overtube connection and a corewire connection each connected to a support structure supporting a control element with an adjustable channel. In some embodiments, the corewire connection comprising a viewing area, such as a window, for observing the corewire. The method comprises guiding the proximal end of the corewire into the overtube connection, the adjustable channel, and the corewire connection until observing the corewire through the viewing area indicating proper placement of the corewire. The method further comprises engaging the corewire connection to grip the corewire extending from the proximal end of the overtube, and engaging the tube connection onto the proximal end of the overtube.

BRIEF DESCRIPTION OF THE DRAWINGS

FIG. 4A is a side view of the torque coupler of FIG. 1 that interfaces the resilient element with the corewire.

FIG. 6 is a sectional view of the fiber cartridge of FIG. 5 taken along the longitudinal axis of the fiber cartridge.

FIG. 7 is a fragmentary view of the fiber cartridge of FIG. 5 in a deployed configuration with only a portion of the flares fibers shown.

FIG. 12 is a top view of an alternative embodiment of an actuation tool.

FIG. 13 is an end view of the actuation tool of FIG. 12.

FIG. 14 is a bottom edge view of the actuation tool of FIG. 12.

FIG. 18 is a side view of a rapid exchange aspiration catheter.

FIG. 18A is a fragmentary expanded view of the catheter of FIG. 18 taken at the position labeled A.

FIG. 18B is a fragmentary expanded view of the catheter of FIG. 18 taken at the position labeled B taken at the tip of the catheter.

FIG. 19 is a top view of the catheter of FIG. 18 in which the view is rotated 90 degrees relative to the view of FIG. 18 to show the curvature of the tip.

FIG. 19A is a fragmentary expanded view of the catheter of FIG. 18 at the orientation of FIG. 19 taken at the position labeled A.

FIG. 19B is a fragmentary expanded view of the catheter of FIG. 19 at the orientation of FIG. 19 taken at the position labeled B taken at the tip of the catheter.

FIG. 20 is a fragmentary side view of an aspiration catheter having a narrow diameter distal segment for placement in small vessels within the body.

DETAILED DESCRIPTION OF THE INVENTION

Figure 1A:
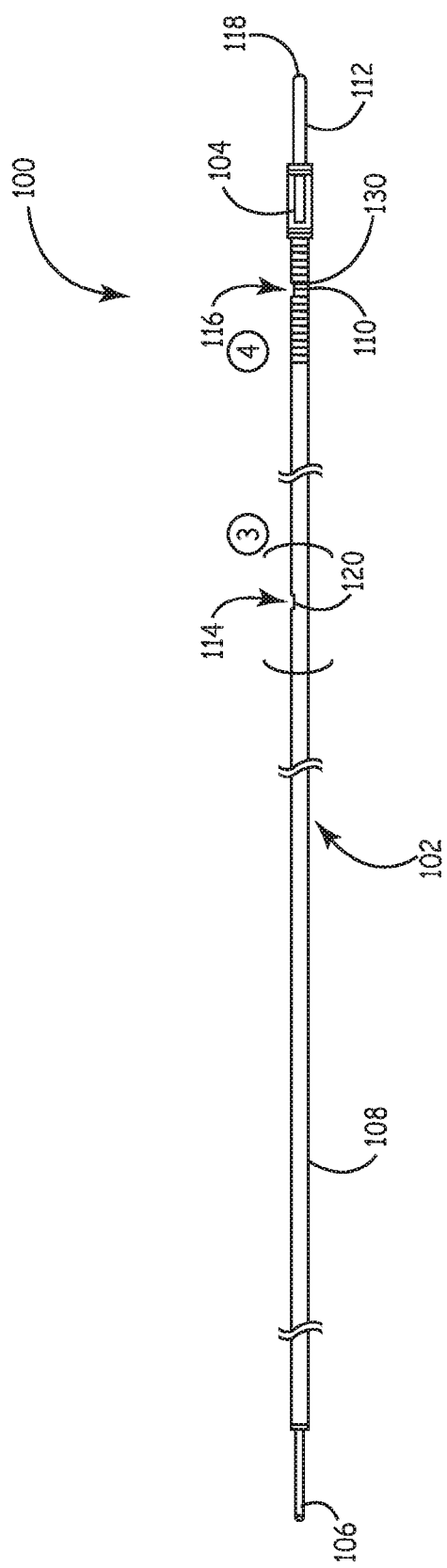
FIG. 1A is a side view of a filter device comprising an integrated guiding device with a fiber cartridge.

A system for effectively trapping and removing emboli and thrombus from vessels of the body, such as blood vessels, generally comprises a fiber-based device and an aspiration catheter, which can be used together, separately and/or with other medical treatment devices. The fiber-based device can interface with an integrated guiding structure that provides for delivery of the device as well as deployment and collapse of the device for recovery. Improved integrated guiding structures described herein provide a torque coupler interfaced with a resilient segment, to improve flexibility and maneuverability of the structure. The fiber-based device, which can function as a filter in some embodiment, can comprise a fiber cartridge with fibers. An improved fiber cartridge can comprise two radiopaque elements or markers that come together when the filter is properly deployed for easier visualization regarding the filter status. An actuation tool can comprise a rotatable element with optional locking element(s) that can be used for controlled movement of a corewire relative to an overtube of the integrated guiding structure, such as to control deployment and/or collapse of a fiber-based element. The actuation tool provides for ease of use as well as designs that reduce the chance of improper loading and improper deployment of the corresponding medical device. The aspiration catheter can have radiopaque bands that are held in place under reinforcing wires embedded into the catheter walls. The secured bands have a reduced chance of catching on structure within a patient's vessel, such as a blood vessel, such that the safety of the procedure is improved. In some embodiments, the aspiration catheter, generally in a rapid deployment format, can have a narrow diameter distal segment for placement of the segment into small diameter vessels, such as blood vessels in the brain.

The devices described herein are generally useful for procedures within vessels of a patient, such as blood vessels. The patients are generally humans, although suitable patients include farm animals, pets and the like. Blood vessels of particular interest include, for example, coronary arteries, saphenous vein grafts (SVG's), carotid arteries, femoral arteries, peripheral arteries and other arteries of the brain. In general, delivery of the devices to selected locations involves tracking the device around various curves and past branches in the vessels. When maneuvering the integrated guiding device within the blood vessel, torque couplers can prevent the components of device from twisting, and resilient elements can help steer the device in the blood vessel. One or more functional medical structures can be delivered over or integrated with the integrated guiding device to treat plaque build up on blood vessel walls. An aspiration catheter can be used to remove the debris that is generated from treating plaque on the blood vessel walls and finally to retrieve the functional medical structure.

In general, the treatment systems described herein comprise a fiber-based system, which can be a filter system, and an aspiration catheter. While these devices can be advantageously used together as a system, the fiber-based element can be used independently or with a different aspiration catheter. Similarly, the aspiration catheter can be used separately to perform thrombectomy procedures without a filter and/or in procedures with different types of filters and/or other medical devices. As described in detail below, the fiber-based device comprises an integrated guide structure with a fiber cartridge mounted on the integrated guide structure, which functions to control deployment and collapse of the fiber cartridge to a lower profile configuration. However, in some embodiments, alternative functional medical components can be mounted on the integrated guide structure for corresponding medical procedures.

The fiber cartridge generally comprises fibers that are within a compact bundle in a delivery configuration, and that flare outward near their centers in a deployed configuration so that the fibers can fill a vessel lumen as a three dimensional filtration matrix. In the fiber device, the fiber cartridge is interfaced with the components of the integrated guide structure in which the movement of the end elements of the fiber cartridge respectively holding fixed the fiber ends are translated relative to each other based on movement of the components of the integrated guide structure.

An integrated guiding structure comprises a corewire and an overtube (e.g. a hypotube or polytube) that receives the corewire. The proximal end of the corewire extends from the proximal end of the overtube. The corewire and the overtube can be provided with additional structure or establish a structural relationship that enables longitudinal movement of the corewire with respect to the overtube, providing communication between the proximal and distal ends of integrated guiding device with the fiber cartridge and/or other functional medical structure located near the distal end of the integrated guiding structure. The integrated guiding device can also comprise one or more torque couplers. For flexibility and steerability, one or more resilient elements can be associated with the corewire or overtube or both.

Torque couplers provide considerable advantages with respect to delivery of the integrated guiding device by rotationally coupling the components and providing desired longitudinal motion of the integrated guiding device. Torque couplers can be used to rotationally couple the corewire with the overtube to reduce or prevent twisting of the corewire relative to the overtube. It has been found the overtube can be rotationally coupled with the resilient element even though the resilient element has a greater elasticity relative to the overtube. Through the use of a torque coupler associated with a resilient member significantly improved torque transmission to the distal end of the integrated guide structure can be achieved. With the components of the integrated guiding device rotationally coupled, the corewire and the overtube can be manipulated or guided to a specific location within the patient through manipulating the portion of the device extending from the patient. Specifically, the torque applied externally to the patient near the proximal end of the integrated guiding structure can be transferred to the distal end of the integrated guiding structure within the patient's vessel.

Torque couplers can be particularly useful for corewires and overtubes with small cross sections. When the corewires and overtubes have such thin cross sections, the corewire can twist, such that torque cannot be efficiently transferred from the proximal end of the integrated guiding structure to the distal end of the corewire without the torque coupler. Torque can be transferred better from the proximal end to the distal end of the integrated guiding device when a torque coupler couples the corewire and overtube to provide torque transmittal, i.e. rotational communication, between the overtube and corewire.

To facilitate steering of integrated guiding device, the flexibility of the overtube can be enhanced by a resilient member, such as a coil or a slotted segment. The properties of the resilient member can be selected to provide the desired degree of flexibility of the structure. In some embodiments, a resilient member is located at or adjacent the distal end of the overtube to provide flexibility for guiding the integrated guide structure through tortuous vessels of a patient. The coil can be welded or otherwise fastened to the overtube with the coil abutting the distal end of the overtube, or the coil can overlap with a distal portion of the overtube, such as a tapered segment of the overtube. In additional or alternative embodiments, a coil pattern can be cut into the overtube to form a resilient element. In some embodiments slotted segments can have the advantages of improved flexibility while providing appropriate levels of mechanical stability since more resilient coils can distort their shape beyond a desired amount. In some embodiments, it can be desired to have both a coil and a slotted segment associated with the overtube in a selected configuration at the distal end of the overtube.

Slotted segments generally comprise a plurality of slots of selected dimensions and orientations. Slots may or may not cut through the overtube, i.e., the slots may be cut to remove material without passing through the full thickness of the material. While the overtube with desired slots, in principle, can be formed from any appropriate method, convenient approaches involve the formation of the slots after the basic structure of the overtube is formed. In some embodiments, two opposing slots can be cut into the overtube, leaving an area of tube between the two opposing slots. Additional pairs of opposing slots can be spaced apart a selected amount from adjacent pairs of opposing slots. In further embodiments, pairs of opposing slots can be rotated, e.g., about 90 degrees, around the circumference of the overtube relative to adjacent pairs of slots. The slot may or may not be cut perpendicular to the central axis of the overtube, and in some embodiments, the slots are cut at a selected angle. The slots can be cut into the overtube using any practical approach, such as laser cutting.

The fiber cartridge comprises a bundle of flexible fibers with a first end secured together, optionally engaged with a first tube and with a second end secured together, optionally engaged with a second tube. The fibers can be surface capillary fibers with lengths appropriate for the size of the vessel. The first end of the fibers is secured to a first radiopaque marker, such as a radiopaue tube, and the second end is secured to a second radiopaque marker, such as a second tube. When the first radiopaque marker and the second radiopaque marker moves toward and away from the other, the bundle of fibers respectively flare into a deployed filter structure and collapse into a low profile configuration. It has been observed for some fiber cartridge embodiments that a twisting of the fiber bundle during the loading of the cartridge leads to more uniform deployment of the fiber structure upon deployment in a vessel. Similarly, the fibers of the fiber bundle can be heated to form a more effective filter element. The deployed fiber cartridge generally can fill a lumen within a body with a three dimensional filtration matrix, although for embolectomy applications, the filtering function may be secondary. The tubes are placed onto the corewire with the corewire extending through the lumen of the short tubes. The first tube is secured to move with the overtube, and the second tube is secured to move with the corewire. The first and second tubes, associated with the fiber cartridge can comprise a radiopaque material to permit x-ray observation of the tubes when they are within the body, although other marker structures/material can be effectively associated with the respective ends of the fiber cartridge. The tubes of the fiber cartridge can have appropriate diameters as well as appropriate selected lengths to permit insertion of at least a portion of one tube into the other tube. The ability to see the markers coming together through visualization in the body provides greater confidence that the fiber cartridge is properly deployed and that the fibers are flared a selected amount.

An actuation tool for the integrated guide structure can be used to provide controlled longitudinal motion of the corewire relative to the overtube to control the configuration of the fiber cartridge or other functional medical structure that is within the patient from outside the patient. Generally, the actuation tool comprises a support structure, a transmission, an overtube connection, a corewire connection, an adjustable channel, and a rotatable element. The actuation tool can be attached to the proximal end of the corewire using the corewire connection and the proximal end of the overtube using the overtube connection. Through the action of the transmission, rotating a rotatable element, such as a dial or lever, produces controlled relative longitudinal motion of the corewire and overtube connections to move the proximal ends of the overtube and corewire relative to each other to operate the integrated guiding device. A lock can stop the rotatable element at the appropriate degree of rotation to properly deploy the filter. The lock can be disengaged, such as through the depression of a button or the like, to collapse the fiber cartridge into a recovery configuration. Another lock element, such as a removable structure, e.g., a clip, can prevent rotation of the rotatable element prior to a selected time to deploy the fiber cartridge. The adjustable channel can be fashioned to provide support for effectively the entire length of the corewire. Specifically, the channel can have a sufficiently small cross section, such that there is nominal clearance between the corewire and the channel.

Generally, an aspiration catheter comprises a tube and an aspiration connection for connection to a suction device. While it can be desirable for the tube to have a single lumen, in some embodiments, the tube can have a plurality of lumen over all or a portion of the length of the tube. An aspiration catheter can be used to retrieve the fiber cartridge and/or to aspirate thrombus or debris generated from treating the vessel. To facilitate positioning of the distal end of the catheter near the selected position in the vessel, one or more radiopaque bands are mounted near the distal end of the catheter to permit x-ray observation of the position of the catheter within the body. If a plurality of radiopaque bands is used, they can be located along different portions of the tube, which can provide further indication of position and orientation of portions of the catheter within the body. In some embodiments, the catheter body is formed of polymer, and metal wire, which can be formed into a mesh or the like, which is embedded into the polymer to provide a desired amount of mechanical strength while providing appropriate flexibility. In improved embodiments described herein, the metal wire, such as a metal sleeve, can be provided over the radiopaque band(s) to secure the radiopaque band and reduce the possibility of the radiopaque band catching onto structure within the vessel, such as a stent or thrombus, which can complicate the procedure and can result in the removal of the band from the catheter. The metal sleeve can comprise of interwoven wires, a coiled wire or the like.

With respect to the selection of catheter size, a larger catheter provides a corresponding increase in the ability to aspirate fluid from the vessel while a desire to enter into smaller vessels limits the size of the catheter since larger catheters cannot be maneuvered into smaller vessels and can excessively block flow within smaller vessels. In some embodiments described herein, the aspiration catheter has a distal segment with a smaller diameter relative to the majority of the catheter tube. These catheter designs provide a better balance of aspiration abilities while providing the capability of entering smaller vessels. Thus, in some embodiments the aspiration catheter can be sized and shaped to enter small blood vessels in the brain for treatment of stroke or other procedures performed in these vessels.

If a fiber-based device is used in a system with the aspiration catheter, the aspiration catheter is generally used as a retrieval catheter to facilitate removal of the fiber-based device from the patient. In particular, aspiration can be applied when the fiber cartridge is being collapsed and/or as the fiber cartridge is drawn into the distal end of the catheter. The use of aspiration results in the capture of emboli inadvertently released from the filter during removal from the vessel. In some embodiments, the fiber cartridge can be used in an embolectomy procedure by dragging an obstruction or thrombus into the catheter by moving the deployed fiber cartridge toward the catheter generally with the use of aspiration. The embolectomy procedure can be performed to remove a blockage from a blood vessel such as in the brain to treat an acute stroke event.

The improved features described above can be used together or individually within a particular medical system. Specifically, an improved fiber-based device can comprise a fiber cartridge that provides for improved visualization of fiber deployment through the use of radiopaque markers bonded to the respective fiber ends. The fiber-based device can have improved manueverability through the use of a torque coupler associated with a resilient member near the distal end of an overtube within the integrated guide structure. An improved actuation tool provided for easier deployment of the filter into a proper configuration and collapse of the fiber-based element for removal from the vessel. The aspiration catheter can be designed with radiopaque bands that are less likely to catch on structure within the vessel. In some embodiments, a reduced diameter distal tip provides for effective delivery of the catheter tip into small vessels, such as blood vessels of the brain, for procedures in small vessels. Thus, these devices can be effective for critical medical procedures.

Fiber-Based Device

The fiber-based devices described herein generally comprise an integrated guide structure and a fiber cartridge with fibers mounted onto the integrated guide structure. The fibers in the fiber cartridge are configured as a bundle with fibers aligned into a low profile configuration for delivery. Upon deployment of the fiber cartridge, the fibers flair outward from near their center into a deployed configuration, generally with the fibers forming a filtering matrix across the lumen of a vessel. The integrated guide structure generally comprises resilient elements to improve maneuverability of the distal end of the device within a patient's vasculature or other vessels, and torque couplers can provide rotational coupling between a corewire and an overtube. Improved maneuverability can be achieved through the integration of a torque couple with a resilient element. The fiber cartridge is coupled between the corewire and the overtube such that relative motion of the devices functions to actuate or de-actuate the fiber cartridge. An actuation tool can be used to significantly facilitate the control of the relative motion of the corewire and overtube using a rotatable element, such as a dial or lever, while reducing or eliminating the chance of kinking the delicate proximal end of the corewire.

FIG. 1A shows an embodiment of a fiber-based device 100 comprising an integrated guiding device 102 with a fiber cartridge 104. The integrated guiding device comprises a corewire 106, overtube 108, a first resilient element 110, a second resilient element 112, a first torque coupler 114, and a second torque coupler 116. Corewire 106 extends through a central lumen of overtube 108 with the distal end and the proximal end of the corewire extending from the overtube. First resilient element 110 covers a portion of corewire 106, and first resilient element 110 can extend from the distal end of overtube 108 or overlap with a portion of the distal end of overtube 108. First resilient element 110 attaches near its distal end to the proximal end of the fiber cartridge 104. Second resilient element 112 is secured to corewire 106 at or near the distal end of the device, for example, with adhesive or by welding. In particular, a welded tip 118 can be placed at the distal tip of corewire 106. Torque couplers 114, 116 have appropriate structure, described further below, to rotationally couple corewire 106 with overtube 108 and corewire 106 with first resilient element 110, respectively.

Figure 1B:
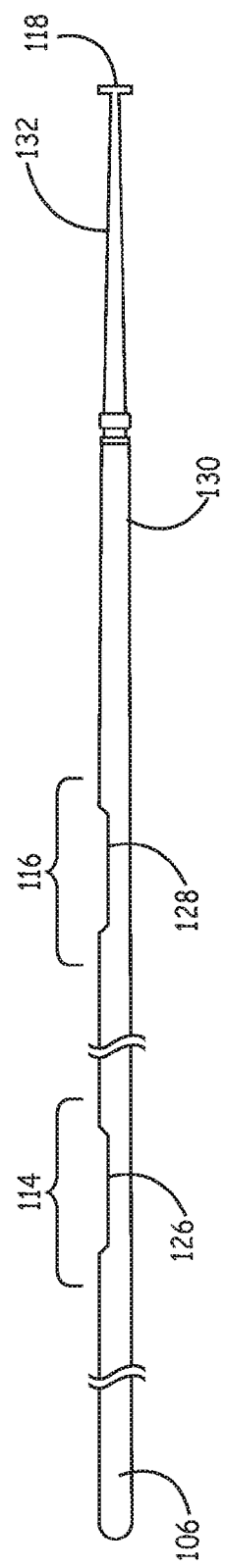
FIG. 1B is a side view of the core wire of the filter device of FIG. 1A separate from the remaining components of the filter device.

Referring to FIG. 1B, corewire 106 is shown separated from overtube 108, second resilient element 112 and fiber cartridge 104. Corewire 106 has a first flattened section 126 and a second flattened section 128 that form keyways for torque couples 114, 116, respectively. Distal segment 130 is tapered, and a distal tip 132 is flattened along a portion over which second resilient element 112 is placed. Weld 118 is located at the distal tip of corewire 106. In some embodiments, corewire 106 can have one or more deliberate notches, such as in the proximal half of the corewire, to provide for a controlled slight amount of friction between the corewire and overtube.

The resilient elements provide segments of greater flexibility relative to the overtube flexibility. It is desirable for the distal end of the fiber-based device to have greater flexibility for navigating bends and branches along the vessels. In general, a resilient member has an overall tubular shape with a central lumen for the passage of the corewire. In general, the increased flexibility of the resilient member is achieved through a structure that lacks a solid uniform wall. Also, decreasing the wall thickness at or near the distal end provides increased flexibility. For example, the wall thickness can be machined down, and a polymer jacket, such as a heat shrink polymer, can be placed over the thinned wall to maintain an approximately uniform outer diameter as well as smoothing out potential edges. For example, resilient elements can comprise a coil and/or the tube with a coil pattern or slots cut into and/or through the tube. While flexibility is desired in the resilient section, elongation and stretching are not desired. Also, it is desired that the resilient elements have a construction such that torsional force can be transferred without significant loss along the length of the section. The transfer of torsional force enhances steerability of the tip and maintains any twist that has been imparted into the fiber cartridge. As a result, if a coil or other appropriate resilient structure is used, the resilient element can be rotationally locked to a portion of the corewire such as by creating circumferential mechanical interference between the two members.

As shown in FIG. 1A, second resilient member 112 is a coil that is secured between fiber cartridge 104 and weld 118. In alternative embodiments, the coil can be replaced with a portion of cut tubing or a combination of cut tubing and one or more coil(s). Similarly, first resilient member 110 can be a coil secured between fiber cartridge 104 and overtube 108. Resilient member 110 can be attached directly, or indirectly with a spacer or the like, to the distal end of overtube 108, or resilient member 110 can overlap with a portion, such as a tapered portion, of overtube 108. As with second resilient member 112, first resilient member 110 can comprise cut tubing or a combination of cut tubing and one or more coils, as an alternative to a coil.

Figure 2A:
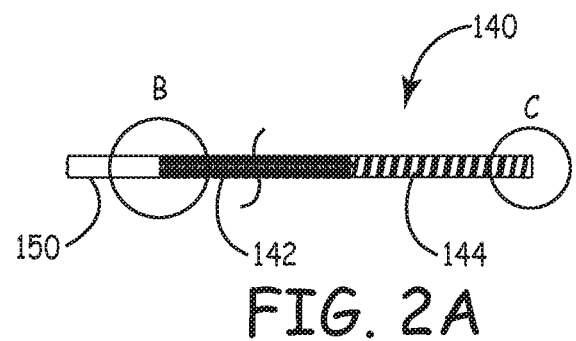
FIG. 2A is a fragmentary side view of an alternative embodiment of a resilient element comprising cut tubing with a section of cut slots and a spiral cut section.
Figure 2B:
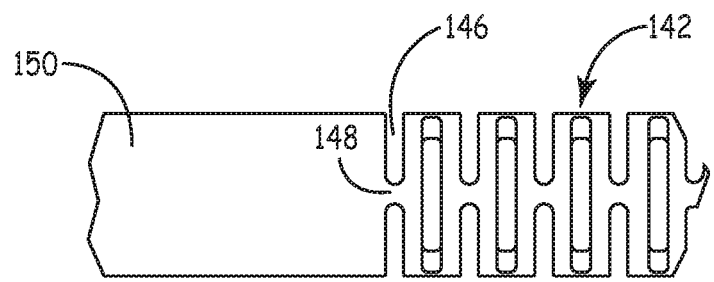
FIG. 2B is an expanded fragmentary view of the resilient element with cut slots adjacent an uncut section of the overtube in which the view is taken at the B marked portion of FIG. 2A.
Figure 2C:
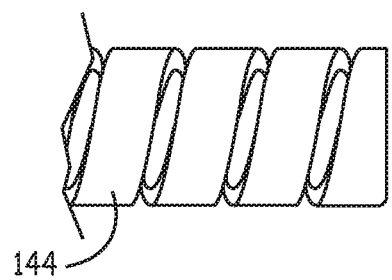
FIG. 2C is an expanded fragmentary view of the spiral cut portion of the resilient element in which the view is taken at the C marked portion of FIG. 2A.

The inner diameter of the resilient members should be at least large enough to accept the corewire. The outer diameter generally is similar to the outer diameter of the overtube. A person of ordinary skill in the art can select the dimensions and elasticity of the coil to yield desired degrees of flexibility. A particular embodiment of cut tubing suitable to replace a coil, especially for first resilient member 110, is shown in FIG. 2A. Referring to FIG. 2A, resilient member 140 comprises a first section 142 with cut slots and a second section 144 with a spiral cut, which then has characteristics similar to a coil. Referring to FIG. 2B, first section 142 comprises pairs of opposing slots 146 are cut through the tube with rails 148 connecting the opposing slots. Pairs of adjacent opposing slots are rotated about 90 degrees relative to each other. The dimensions and spacing of the slots can be selected to achieve desired resiliency. As shown in FIG. 2B, resilient member 140 is cut into overtube 150 such that they are integral members of the structure. Referring to FIG. 2C, second section 144 has a spiral cut. The spiral cut provides for a slight expansion of the inner diameter to insert a short tube of a fiber cartridge within the inner diameter of second section 144. In some embodiments, first section 142 generally can be many inches long, while second section 144, can be a fraction of an inch in length.

Suitable cutting techniques for cutting an overtube include, for example, mechanical cutting, electrostatic discharge machining (EDM), cutting with high pressure fluids, chemical etching and laser cutting. Laser cutting can be particularly efficient for the formation of a significant number of precision cuts using automated control, especially cuts that penetrate through the catheter/tube to the inner lumen. Etching may be particularly effective to form slots that do not penetrate through the material of the overtube.

Further detail on resilient members are disclosed in published U.S. patent application 2006/0200047A to Galdonik et al., filed Mar. 4, 2005, entitled "Steerable Device Having A Corewire Within A Tube and Combination With A Functional Medical Component," which is incorporated herein by reference.

The length of overtube 108, e.g., a hypotube or a polytube, can generally be selected for the particular application. For example, for intervention in the aorta, the overtube generally would have a length from about 190 cm (63 inches) to about 300 cm (106 inches). The cross section of the overtube can be characterized by an inner diameter and an outer diameter. The inner diameter general ranges from about 0.001 inches to about 0.01 inches, in further embodiment from about 0.003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 inches to about 0.011 inches and in other embodiments from about 0.015 inches to about 0.013 inches, with standard guidewire outer diameters being about 0.014 inches. The corewire has a diameter just slightly less than the inner diameter of the tube by about 0.001 inches to about 0.003 inches. A person of ordinary skill in the art will recognize that additional ranges within the explicit ranges for the diameters are contemplated and are within the present disclosure.

In general, corewire 160, overtube 108 and resilient elements 110, 112 can be formed from one or more of various materials, such as polymers, metals and combinations thereof. The overtube and corewire may or may not be formed from the same material. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy.

Suitable polymers include, for example, synthetic polymers as well as purified biological polymers and combinations thereof. Suitable synthetic polymers include, for example, polyamides (e.g., nylon), polyesters (e.g., polyethylene teraphthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

In other embodiments, the surface of the corewire, the inner surface of the overtube, the outer surface of the overtube, portions thereof or combinations thereof is coated with a friction reducing agent. Suitable friction reducing agents include, for example, suitable polymers, such as polytetrafluorethylene, i.e., Teflon® or a polymer coating such as parylene. The coating of the corewire or a portion thereof can facilitate relative longitudinal motion of the corewire relative to the overtube.

Torque Couplers

Torque couplers generally provide at least temporary torque coupling between a corewire and an overtube of an integrated guide structure without preventing at appropriate times a desired amount of relative longitudinal motion of the overtube and the corewire. Various designs of torque couplers can accomplish this objective. In embodiments without torque coupling, due to the very thin nature of the components of the integrated guiding device, torque applied at the proximal end can fade as a result of components being twisted, such that the amount of rotation at the distal end is less than desired relative to the rotation at the proximal end. The corewire, tube, and resilient element can contribute to an integrated guiding device with a small cross section, producing poor transfer of torque from the proximal end to the distal end of the corewire. However, by coupling the rotational motions of these components, the rotation of the distal end of the corewire can be better controlled in the coupled system upon rotating the tube at the proximal end.

In some embodiments the rotational coupling extends along the entire length of the tube. However, in further embodiments, the rotational engagement provided by a torque coupler can be constrained for convenience to localized regions such as at or near the distal end of the overtube, at or near the proximal end of the overtube, and/or in the central region of the overtube. Generally, it is advantageous to couple the tube and corewire in a distal-most region if the desired goal is efficient transfer of torque to the distal tip. In particular, it can be desirable to have rotational coupling between the overtube and the corewire within twenty centimeters of the distal end of the corewire, and in some embodiments, within about four centimeters from the distal end of the overtube.

Furthermore, additional rotational coupling provided by additional torque couplers can further improve torque transmission to the distal end of the corewire. In particular, it has been found to be advantageous to provide a torque coupler integrated with a resilient member associated with and extending from the distal end of the overtube. Since the resilient member can extend over a significant distance, the incorporation of a torque coupler within the resilient element provides for the placement of a torque coupler closer to the distal end of the corewire without correspondingly making the resilient member smaller. Surprisingly, even though the resilient element is resilient, the resilient element can be effectively adapted to form a component of a torque coupler for transmission of torque between the corewire and the resilient element, and the attachment of the resilient element to the overtube further provides rotational coupling among the various elements of the fiber-based device. For resilient members that are a coil, it can be desirable to fuse some of the turns of the coil together at the torque coupler, which does not significantly change the resilient nature of the element while stabilizing the function of the torque coupler. In one particular embodiment, an approximately 2.25 mm section of a coil is fused with a laser at the location for the formation of the torque couple, although other segment lengths can be selected as long as the flexible nature of the coil is not significantly changed and other techniques can be used to fuse a section of the coil at the torque coupler.

Torque couplers are generally formed by components of the integrated guiding device engaging with each other. In some embodiments, the components engage by the mechanism of a protrusion fitting within a depression. Specific torque coupling embodiments are shown in FIGS. 1, 3 and 4. FIG. 1A shows an assembled fiber-based device 100 comprising an integrated guiding device with portions of torque couplers 114, 116 shown as indentations or notches 120, 130 in overtube 108 and first resilient element 110, respectively. These indentations 120, 130 form keys or key-like structures which engage with the flattened keyway portions 126, 128 formed in the corewire 106 as shown in FIG. 1B.

Figure 3A:
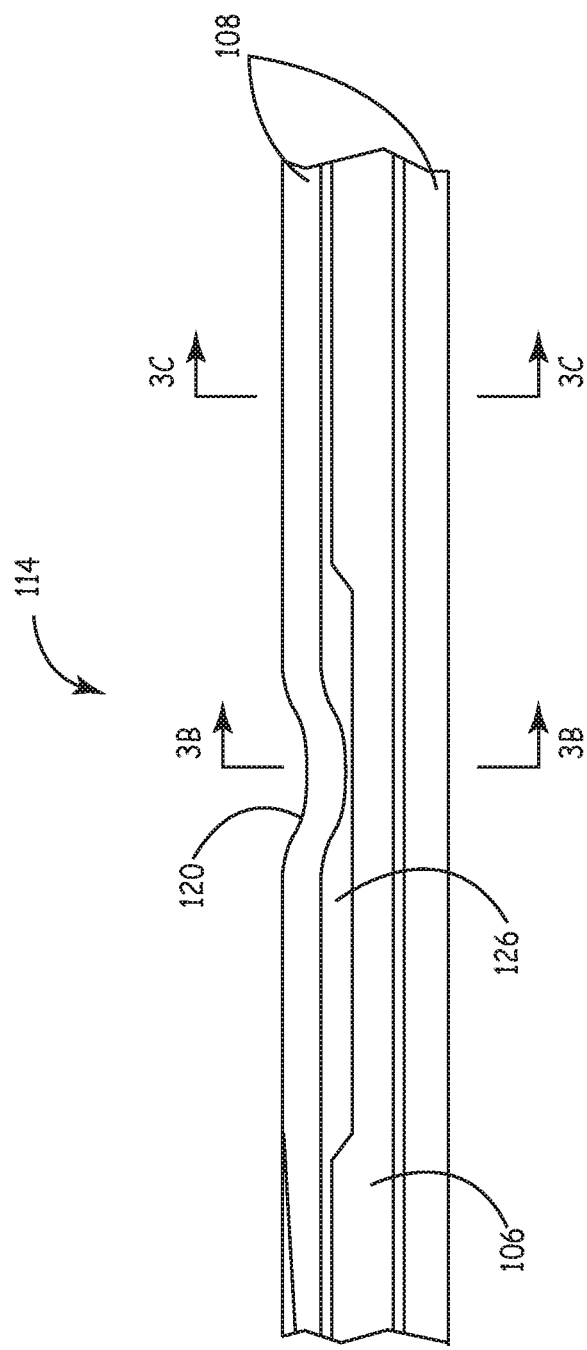
FIG. 3A is a side view of the torque coupler of FIG. 1 that interfaces the overtube with the corewire.
Figure 3B:
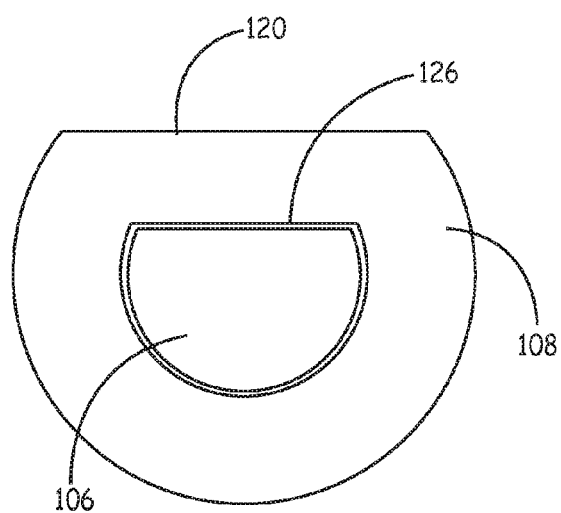
FIG. 3B is a sectional view of the torque coupler taken at line 3B-3B in FIG. 3A.
Figure 3C:
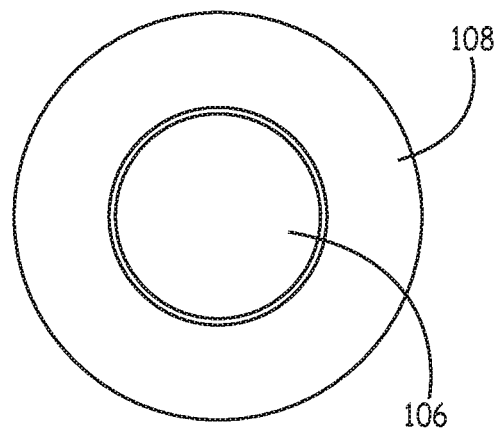
FIG. 3C is a sectional view of the corewire and the overtube taken outside the torque coupler at line 3C-3C of FIG. 3A.

Referring to FIG. 3A, first torque coupler 114 rotationally couples corewire 106 with overtube 108. The walls of overtube 108 comprise an indentation 120 on the outer surface defining a downward protrusion along the inner diameter that fits into flattened keyway portion 126 on the outer surface of corewire 106. The length of flattened keyway portion 126 specifies limits on the relative longitudinal motion of the corewire relative to the overtube. FIG. 3B shows a sectional view of the integrated guiding device taken along torque coupler 114, which is shown as flattened areas interfacing each other due to structure from indentation 120 and flattened keyway portion 126. As a comparison, FIG. 3C shows a sectional view of the integrated guiding device taken along an area outside torque coupler 114. One of ordinary skill in the art would recognize that overtube 108 and corewire 106 can have different shapes for the cross sectional interface regardless of whether the sectional view is taken at the torque coupler or at an area outside the torque coupler.

Figure 4B:
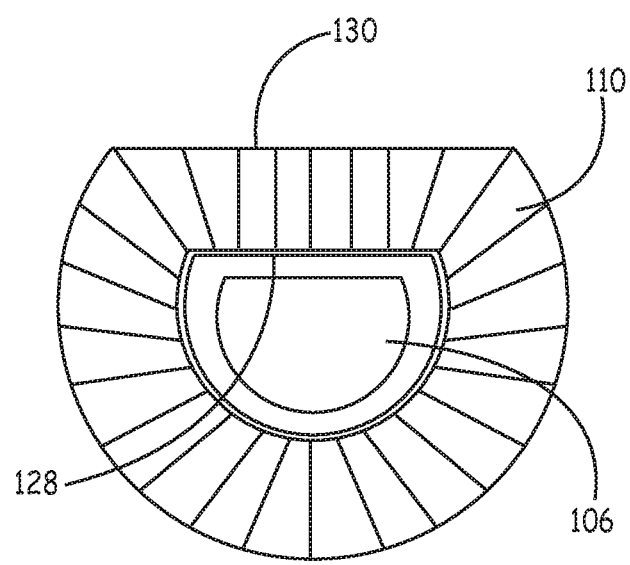
FIG. 4B is a sectional view of the torque coupler taken at line 4B-4B in FIG. 4A.
Figure 4C:
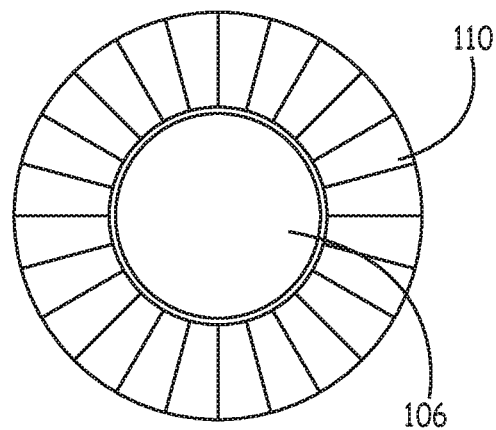
FIG. 4C is a sectional view of the corewire and the resilient element taken outside the torque coupler along line 4C-4C of FIG. 4A.

Referring to FIGS. 4A-4C, expanded sectional views are displayed for second torque coupler 116. Referring to FIG. 4A, torque coupler 116 rotationally couples the corewire 106 with resilient element 110. If the resilient element 110 comprises a coil, a section of coil has an indentation 130 defining a downward protrusion along the inner diameter of the coil that fits into flattened keyway portion 128 of corewire 106. The coil covers a section of corewire 106, extending from roughly the distal end of the overtube 108 to roughly the proximal end of the fiber cartridge 104.

Regardless of whether the resilient element comprises a coil or a cut portion of the overtube, the resilient element is shaped to provide a protrusion that engages with a flattened segment formed in the corewire. The length of flattened keyway portion and the size of the key further constrains the range of lateral motion of the corewire relative to the overtube available without damaging the device, although the fiber cartridge may also provide constraints on the extent of relative lateral motion. FIG. 4B shows a fragmentary sectional view of the integrated guiding device taken through torque coupler 116. Torque coupler 116 has flattened areas engaging each other as a result of the structure of protrusion 130 and flattened keyway portion 128. As a comparison, FIG. 4C shows a sectional view of the integrated guiding device taken along an area outside torque coupler 116 along resilient element 110. In contrast to the semi-circular cross section of the corewire in FIG. 4B, the sectional view taken outside torque coupler 116 has a circular cross-section. One of ordinary skill in the art would recognize that coil 110 and corewire 106 can have different cross sectional shapes as long as the elements are mated to engage properly while providing for some relative lateral movement. There are significant advantages to having a torque coupler interfaced with the resilient member. While the resiliency of the resilient member affords the flexibility to provide for the steering of the fiber-based device, it also causes the resilient member to distort in shape, which decreases the torque transfer from the proximal end to the distal end of the fiber-based device. A torque coupler interfacing the resilient member with the corewire would rotationally couple the resilient member with the corewire to decrease distortion of the resilient member around the corewire and increase the transfer of torque from the proximal end to the distal end of the corewire. Surprisingly, the resiliency of the resilient member does not detract from the ability to function as a torque coupler.

A variety of alternative structures are possible for torque couplers in addition to the lock and key embodiments discussed specifically above. Some alternative embodiments are described in more detail in published U.S. patent application 2006/0200047A, filed Mar. 4, 2005 to Galdonik et al., entitled "Steerable Device Having A Corewire Within A Tube and Combination With A Functional Medical Component," which is incorporated herein by reference.

Fiber Cartridges for Use with Integrated Guiding Device

In general, a fiber cartridge can be combined with an integrated guiding device, to facilitate delivery of a fiber-based element on a structure that provides for delivery of additional treatment devices, such as an angioplasty balloon or a stent delivery device, over the guide structure, which function sin this regard similar to a guidewire. The fiber cartridge can be actuated through the relative longitudinal motion of the corewire and the tube. Generally, the fiber cartridge is located at or near the distal end of the integrated guiding device with control of actuation being provided at the proximal end of the device. In embodiments of particular interest, the fiber cartridge comprises a fibers connected at their respective ends to two separate short tubes. The inner diameter of the short tubes is selected such that the corewire can pass through the central lumen of the short tubes. For deployment, a bundle of the fibers can be in a stacked linear configuration with the short tubes spaced apart such that the fiber bundle has a small profile. Upon deployment, the short tubes are pulled together such that the fibers flare outward from roughly their center to form a filtration matrix across the diameter of the vessel. In some improved embodiments, the short tubes comprise a radiopaque material and are configured to touch or overlap in the deployed configuration to improve visualization of the fiber cartridge deployment during a procedure. Alternatively or additionally, other radiopaque structures or materials, such as an adhesive with a radiopaque composition, can be associated with the fiber ends within the fiber cartridge.

Fibers with non-circular cross sections, e.g., oval, are particularly desirable for use in fiber cartridges. In particular for appropriate embodiments, while not wanted to be limited by theory, it is believed that non-circular fibers pack into a filtration matrix with improved filtration capability with respect to collecting particles with a range of particle sizes while maintaining good flow through the filter even when the filter has captured debris within the vessel. In particular, fibers with surface capillary fibers can be effectively used in fiber-based devices for filtering applications. Fibers with surface capillaries have a non-circular cross section with a more complex geometry. Filters formed with surface capillary fibers have been found to have excellent performance in clinical use, as has been demonstrated in clinical trials with the Fibernet® device from Lumen Biomedical Inc.

Figure 5:
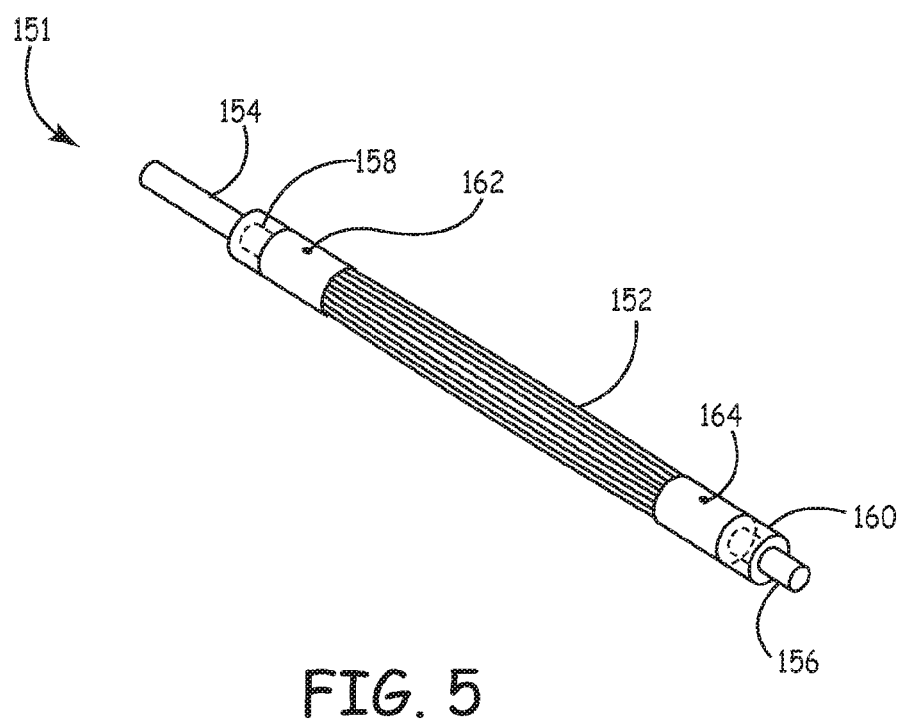
FIG. 5 is a perspective view of the fiber cartridge from the filter device of FIG. 1 separated from the other components.

Referring to FIGS. 5 and 6, an embodiment of a fiber cartridge 151 comprises a bundle of fibers 152, a first tube 154 and a second tube 156. Fiber bundle 152 has a first bonded end 158 bonded to the outer surface of first tube 154 and a second bonded end 160 bonded to the outer surface of second tube 156. Optionally, a first outer band 162 surrounds at least a portion of first bonded end 158, and/or a second outer band 164 surrounds at least a portion of second bonded end 160. The center of the fiber bundle remains unconstrained such that the fibers ran flare outward upon deployment. If the fibers comprise a thermoplastic material, the ends of the fibers can be melt bonded to secure bonded ends 158, 160 to tubes 154, 156, respectively. Additionally or alternatively, an adhesive can be applied at bonded end 158, 160 to contribute to the bonding of the fibers together at the ends as well as to bond the fiber ends to the tubes.

In some embodiments, first tube 154 extends from both ends of first bonded end 158, and second tube 156 extends from both ends of second bonded end 160. In these embodiments, a section of tubes 154, 156 extends into the portion of the fiber cartridge with unbound fibers. The portion of the tubes extending longitudinally outward from the fiber cartridge can be used to secure the fiber cartridge within the fiber-based device as described further below. Tubes 154, 156 should have an inner diameter larger than the diameter of the corewire of the fiber-based device such that fiber cartridge 151 can be loaded over the corewire for incorporation into the fiber-based device.

During deployment of fiber cartridge 151, first bonded end 158 and second bonded end 160 are drawn toward each other on the corewire, as shown in FIG. 7. When tubes 154, 156 move toward each other, the bundle of fibers flare into a three dimensional filtration matrix 170 having a configuration to catch emboli, as shown in a fragmentary view in FIG. 7. The tubes 154, 156 can have different inner and outer diameters to enable one of the tubes to be inserted within the other tube when brought together. In some embodiments, the tubes have a tip configuration to provide for relative insertion that is different from the diameter or shape of the remaining portion of the tube, although the tube diameter can be constant. The bundle of fibers can flare generally to fill the lumen of the vessel in which the fiber-based device is inserted. When one or both of the tubes move away from the other, the bundle of fibers reverts to a lower profile retrieval configuration approximating the initial bundle configuration prior to deployment.

First tube 154 and second tube 156 can be made of radiopaque material to provide observation of the tubes when they are inside the lumen of the body vessel. The radiopaque material allows the tube(s) to be observed using electromagnetic radiation, such as x-ray. Suitable radiopaque materials are discussed above. Thus, for embodiments in which tubes 154, 156 engage following proper deployment, the configuration of the fiber cartridge can be checked within the patient. This is especially helpful in determining whether the fibers are in a properly deployed configuration prior to continuing with the procedure in the vessel. If x-ray observation reveals that the image of the tubes overlap, then the fiber cartridge has been deployed the desired amount. If x-ray observation reveals that tubes are away from each other, then the fiber cartridge is not in the desired deployed configuration, and the physician can attempt to correct the deployment prior to continuing with the procedure. If the procedure is continued with the fiber cartridge not deployed in the proper configuration, then emboli generated in the procedure can more likely escape past the deployed fiber cartridge into the down stream narrowing blood vessels.

It can be difficult to judge the distance between the tubes through x-ray observation, especially during the pressures of procedure. Thus, by making one of the tubes insertable within the other tube, a physician can proceed with confidence in the x-ray observation of the device with the tube merged into a single image, and the chance of error during the procedure can be significantly reduced with a corresponding improvement in the cumulative outcomes of the procedures. Since these devices can be used in significant vessels such as coronary arteries, carotid arteries and smaller arteries of the brain, diminishing the chance of emboli migration that can result in infarctions provides a significant advance in patient care.

Figure 8A:
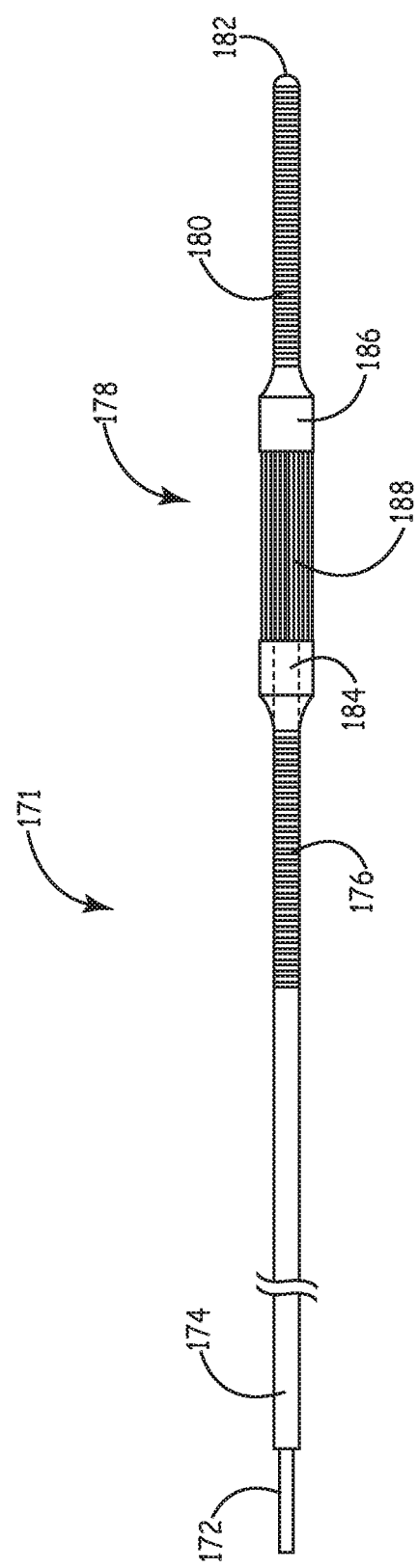
FIG. 8A is a side view of an alternative embodiment of a filter device with a fiber cartridge in a delivery configuration.
Figure 8B:
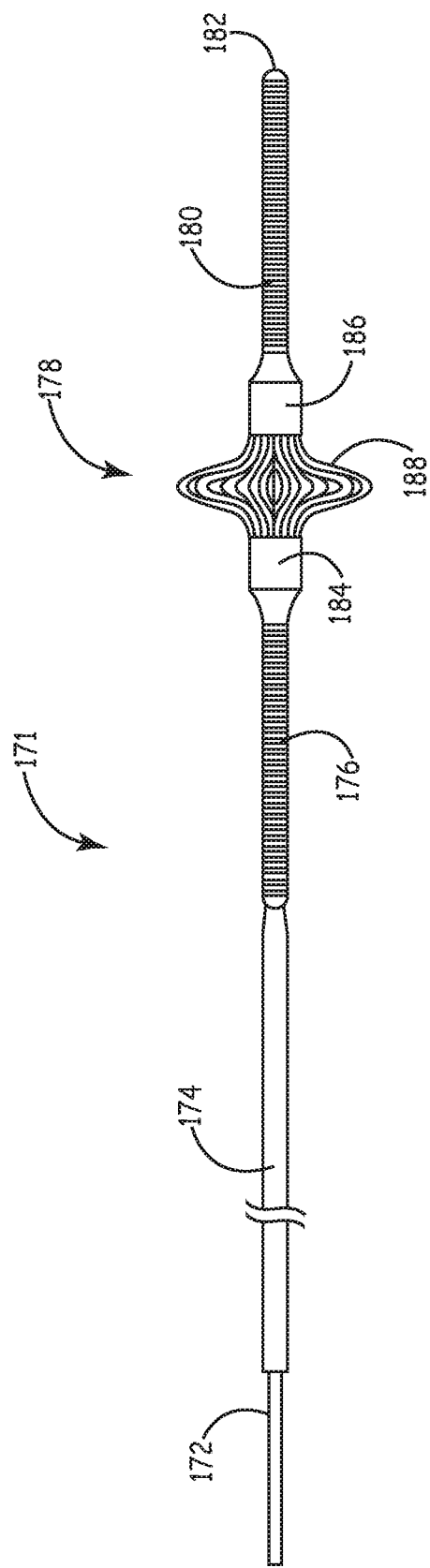
FIG. 8B is a side view of the filter device of FIG. 8A with the fiber cartridge in a flared configuration.

The transition of the fiber cartridge from a delivery configuration to the deployed configuration is shown in FIGS. 8A and 8B, for a fiber-based device 171 similar to the fiber-based device 100 of FIG. 1. Referring to FIGS. 8A and 8B, fiber-based device 171 comprises corewire 172, overtube 174, proximal resilient member 176, fiber cartridge 178, distal resilient member 180 and distal tip 182. Fiber cartridge comprises proximal bonded end 184, distal bonded end 186 and fiber-based element 188. The relative motion of corewire 172 and overtube 174 can be used to deploy the fiber cartridge from a confined narrow profile configuration with the fibers in an aligned bundle for delivery (FIG. 8A) to a deployed configuration at which the filter cartridge is extended radially relative to the axis of the device with the fibers flared out into a fiber matrix, such as a filter matrix, within the vessel (FIG. 8B).

With respect to the fiber bundle, the number of fibers in the bundle generally depends on the desired degree of filtration as well as the thickness of the fibers. In general, the number of fibers can be range from at least 10 fibers, in further embodiments from 25 fibers to 1,000,000 fibers, in other embodiments from 50 fibers to 10,000 fibers and in additional embodiments, from 100 fibers to 5,000 fibers. The length of the fibers can be selected based on the size of the corresponding vessel. When deployed, the centers of the fibers are projected across the lumen of the vessel. Thus, the unconstrained length of the fibers between bonded ends 158, 160 should be at least double the radius of the vessel. In some embodiments relating to the use of a plurality of fibers to expand within the lumen of a patient's vessel, it is generally appropriate to use fibers that have a length from about 2.2 to about 10 times the vessel radius, in some embodiments from about 2.4 to about 5 times the vessel radius and in further embodiments from about 2.6 to about 4 times the vessel radius. For placement in a human vessel, the fibers generally have a length from about 0.5 mm to about 100 mm, in other embodiments from about 1 mm to about 25 mm, and in further embodiments from about 2 mm to about 15 mm. A person of ordinary skill in the art will recognize that additional ranges of fiber numbers and fiber length within the explicit ranges are contemplated and are within the present disclosure.

As used herein, SCF fibers refer broadly to fibers having channels or capillaries along the surface running generally along the length of the fiber or a portion thereof. Fibers have their usual meaning as structures with a length that is significantly larger than the dimensions along a cross section perpendicular to the length. The capillaries can run along substantially the entire length or a fraction thereof. Due to the presence of the capillaries, a cross section through the fiber at the capillary(ies) has a shape with an edge having changing curvatures.

SCF fibers for use in the medical devices are generally formed from biocompatible polymers. SCF fibers can be fabricated from synthetic polymers as well as purified biological polymers and combinations thereof. Suitable synthetic polymers include, for example, polyamides (e.g., nylon), polyesters (e.g., polyethylene teraphthalate), polyacetals/polyketals, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones, ethylene vinyl acetates, polysulfones, nitrocelluloses, similar copolymers and mixtures thereof. Based on desirable properties and experience in the medical device field, suitable synthetic polymers include, in particular, polyether ether ketones, polyacetals, polyamides (e.g., nylons), polyurethanes, polytetrafluoroethylene, polyester teraphthalate, polycarbonates, polysulfone and copolymers and mixtures thereof.

Bioresorbable synthetic polymers can also be used such as dextran, hydroxyethyl starch, derivatives of gelatin, polyvinylpyrrolidone, polyvinyl alcohol, poly[N-(2-hydroxypropyl) methacrylamide], poly(hydroxy acids), poly(epsilon-caprolactone), polylactic acid, polyglycolic acid, poly (dimethyl glycolic acid), poly(hydroxy butyrate), and similar copolymers. Based on experience in the medical field, suitable resorbable polymers include, in particular, polylactic acid, polyglycolic acid, and copolymers and mixtures thereof.

Appropriate polymers also include biological polymers. Biological polymers can be naturally occurring or produced in vitro by fermentation and the like. Suitable biological polymers include, without limitation, collagen, elastin, silk, keratin, gelatin, polyamino acids, cat gut sutures, polysaccharides (e.g., cellulose and starch) and mixtures thereof. Biological polymers generally are bioresorbable. Purified biological polymers can be appropriately formed into a polymer material for further processing into fibers.

The properties of the surface channels and the corresponding cross-section of the fiber generally depend on the process used to form the fibers. One approach for forming a fiber with surface capillaries is described in U.S. Pat. No. 5,200,248 to Thompson et at (hereinafter the '248 patent), entitled "Open Capillary Channel Structures, Improved Process For Making Capillary Channel Structures, And Extrusion Die For Use Therein," incorporated herein by reference. The Background section of the '248 patent additionally references a variety of alternative embodiments of approaches for forming fibers with surface channels or capillaries. Additional approaches for the formation of surface capillaries for use in a fiber-based devices are described in published U.S. Patent application 2005/0209631 to Galdonik et al., entitled "Steerable Device Having a Corewire Within a Tube and Combination With a Functional Medical Component," incorporated herein by reference. Any of these approaches can be used to form surface capillary fibers. In particular, the fibers formed by the process of the '248 patent itself have desirable characteristics and versatility. Further characterization of the SCF fibers, such as with respect to capillary properties, can borrow from the approaches outlined in the '248 patent.

As with the fiber length, the thickness of the fibers can be selected appropriately for the particular use of the fiber. Fiber thickness can be measures in several ways. For example, the radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude. Also, in the fiber field, a pragmatic way has been developed to characterize fiber thickness without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 50 microns to about 5 millimeter, in further embodiments from about 100 microns to about 2 millimeters, and in additional embodiments from about 150 microns to about 1 millimeter. As measured in denier, SCF fibers can have sizes ranging from about 0.1 denier to about 1000 denier in size, in additional embodiments from about 0.5 denier to about 250 denier, in some embodiments from about 1.0 denier to about 200 denier, in other embodiments from about 2.0 denier to about 100 denier and in further embodiments from about 3.0 denier to about 50 denier. A person of ordinary skill in the art will recognize that additional ranges of fiber thickness in diameter measurements or in denier are contemplated and are within the present disclosure.

In general, a commercial device will have a plurality of available sizes such that a physician can select a particular device based on the size of the vessel for treatment. Each size of device can be designed to operate in vessels with a range of sizes. For example, the commercial products can have two sizes, three sizes, four sizes or more than four sizes. In one specific embodiment, the device comprises 480 of 6 denier SCF fibers in a bundle and a crossing profile of 0.033 inches (2.5 French).

It has been found that particular preparation processes for the fibers can lead to significantly improved uniformity of the performance of the fiber-based device. In particular, the fibers are twisted within the fiber bundle. In some embodiments, heat is also applied to the fibers. While any degree of twist can be desirable, twist can be applied to the fiber bundle of at least about 5 degrees and in further embodiments from about 180 degrees to about 360 degrees. Furthermore, multiple rotations, for example, about 360 degrees to about 1080 degrees, can further act to increase the density of fibers and may be advantageous. A person of ordinary skill in the art will recognize that additional ranges of twist within the specific ranges above are contemplated and are within the present disclosure. The twist can be applied by fastening one end of the fiber bundle, applying the twist and fastening the other end of the fiber bundle. A suitable torque coupler can facilitate the application of the twist to the fibers since the corewire does not rotate due to tension in the SCF fibers. With the application of a suitable twist, the fiber-based device is observed to perform with essentially uniform performance. Without the application of the twist, some of the fiber devices have been observed to have small gaps in the filtering of the flow upon deployment. Thus, the twist provides for a commercial device with reproducible performance expected for medical devices in practice.

Various other configurations of the embolism protection structure is discussed in published U.S. Patent Application 2006/0200047 to Galdonik et al., entitled "Steerable Device Having A Corewire Within A Tube and Combination With A Functional Medical Component," incorporated herein by reference.

Actuation Tool

Improved actuation tools described herein provide for proper deployment of the fiber-based device while simultaneously providing ease of use for a physician. Because the fiber cartridge structure can serve an important purpose of preventing emboli from traveling away from a treatment site, it is especially significant for proper function that the structure is deployed properly. Actuation tools can be specially designed to longitudinally move the corewire relative to the tube by gripping and moving the proximal ends of the corewire and tube toward and away from each other to deploy and collapse the fiber cartridge. An improved actuation tool comprises a rotatable element, such as a lever or dial, to change the relative longitudinal position of corewire and the overtube. The rotatable element format is both easier to handle and use as well as avoiding any confusion with respect to direction of movement to transition the fiber cartridge. In particular, it was found with linear translating tool that intuitively to deploy the fiber cartridge physicians wanted to push the corewire into the vessel relative to a fixed overtube, which is the opposite of the correct motion. For embodiments in which the rotatable element is a lever, the arm of the lever can be placed within a housing so that the visible portion of the rotatable element is a tab or handle that rotates around an arc.

Referring to FIGS. 8A and 8B, corewire 172 is pulled in a proximal direction relative to overtube 174 to deploy fiber cartridge 178 by bringing proximal bonded end 184 toward distal bonded end 186. Furthermore, the dial can be interfaced with suitable locks to prevent premature deployment of the fiber cartridge as well as locking the fiber cartridge into a deployed configuration while the procedure is underway. The dial can be straightforwardly replaced with a lever that points to the same position as a position mark on the dial.

For the actuation tool to function properly, the corewire and overtube should be properly loaded into the tool. Actuation tool designs described herein provide a stop to indicate that the overtube has been properly loaded such that the overtube can be locked into position within the tool. Correspondingly, the actuation tool can include a viewing area, such as a window, to show that the corewire is loaded within acceptable limits with respect to the properly loaded overtube. Once the corewire is observed within the viewing area, the corewire can be locked into position in the actuation tool. The viewing area can be a window with or without a transparent cover, or just a position extending from the device that provides visualization of the end of the corewire so that observation of the corewire in the viewing area signals that the corewire is appropriately inserted. The corewire is very thin, and can kink easily even if unsupported for even a very short distance. Kinking of the corewire can damage the device in the middle of a procedure with generates undesirable risk to the patient. As described herein, the actuation tool is designed such that no more then about 0.050 inches and in some embodiments no more than about 0.025 inches of the corewire is unsupported by a selected clearance. In some embodiments, the clearance between the corewire and the support structure within the tool is no more than about 0.010 inches, and in further embodiments no more than about 0.0050 inches, and in additional embodiments is no more than about 0.0025 inches. This support can use interconnected elements within the tool such that the wire remains supported at different longitudinal positions relative to the corewire. A person of ordinary skill in the art will recognize that additional ranges of dimensions relating to support of the corewire within the explicit ranges above are contemplated and are within the present disclosure.

Figure 9:
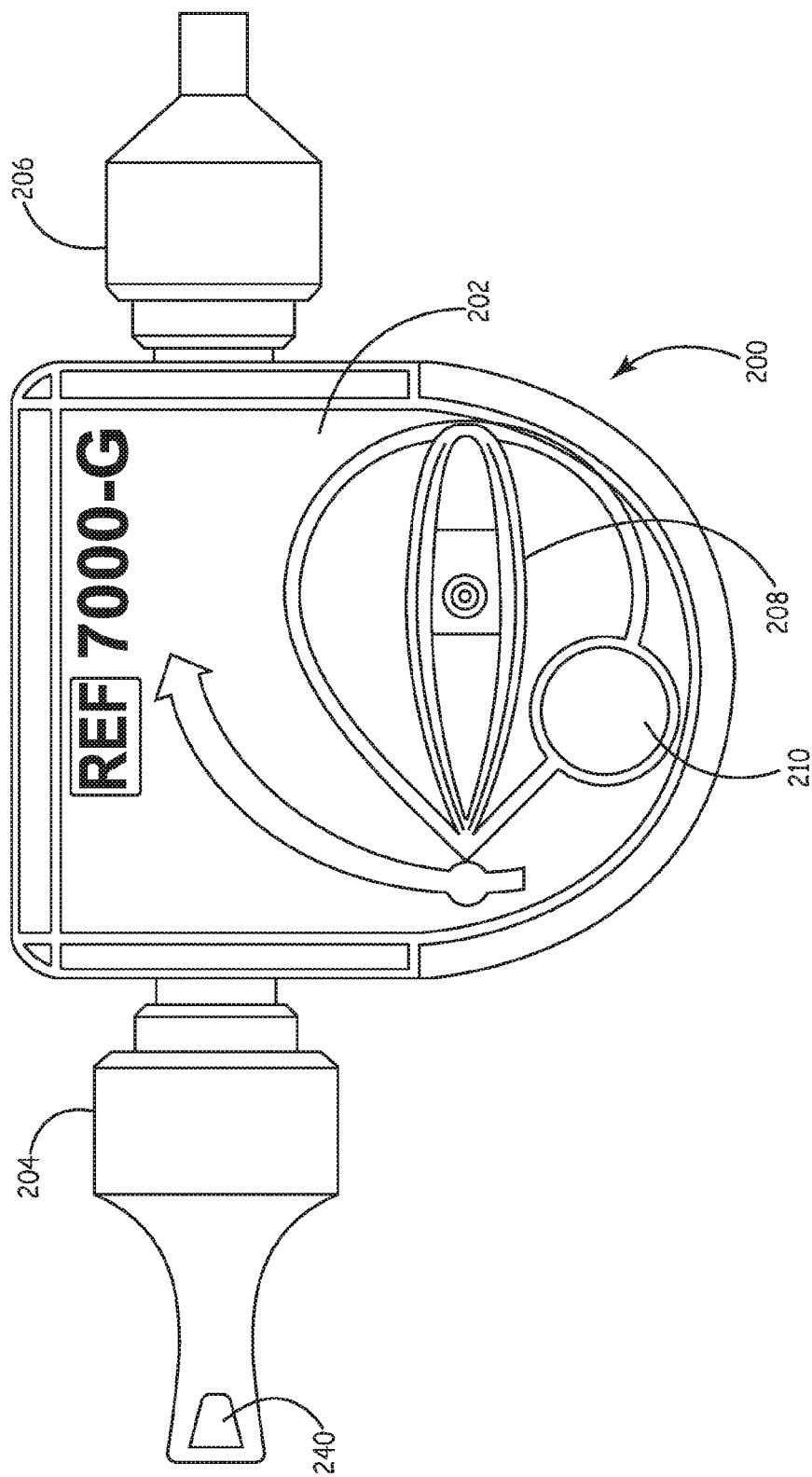
FIG. 9 is a side plan view of an actuation tool for moving the corewire relative to the overtube to control deployment the fiber cartridge.
Figure 11:
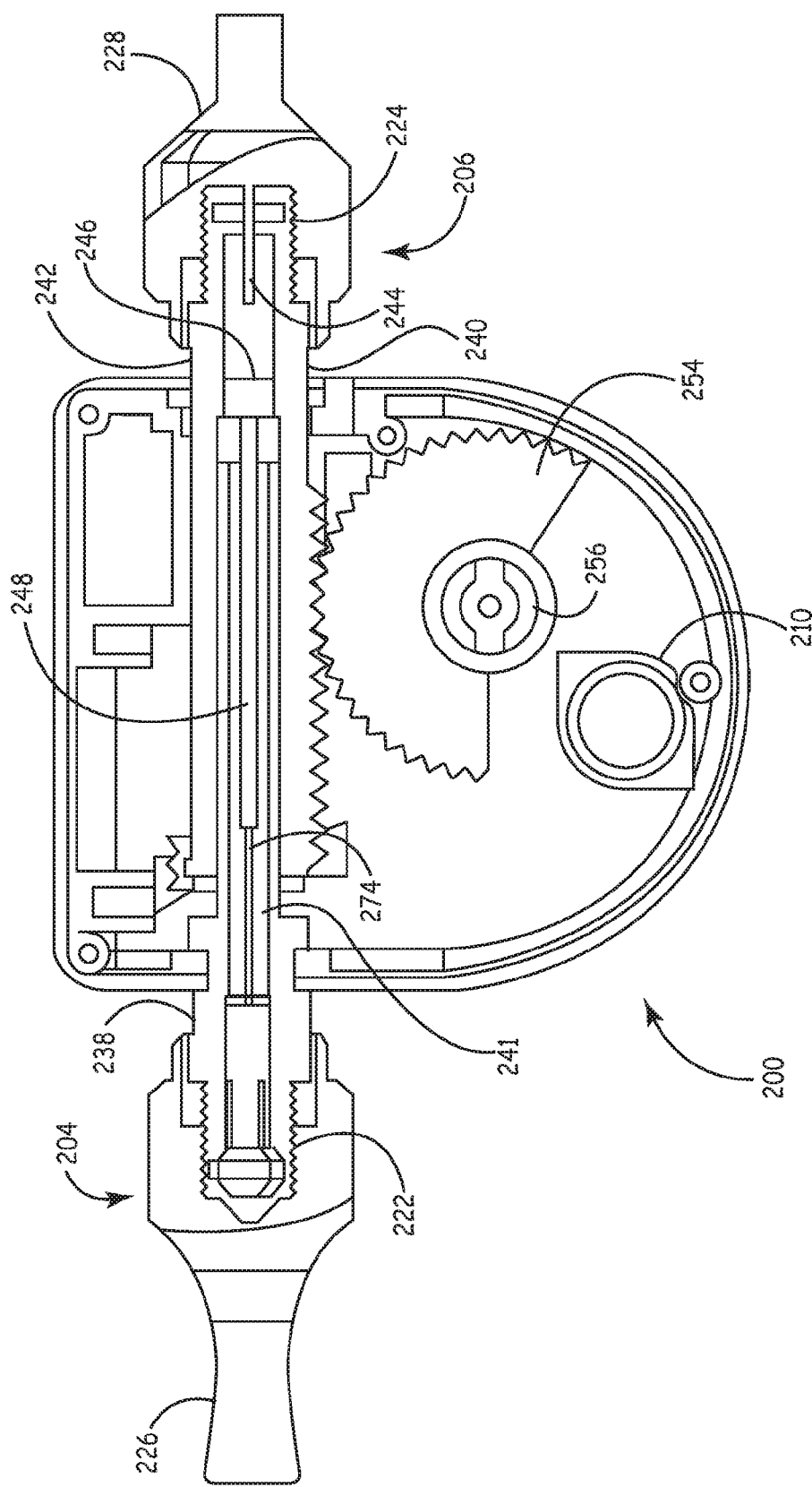
FIG. 11 is a side view of the actuation tool of FIG. 9 with structure removed to expose internal features of the tool.
Figure 15:
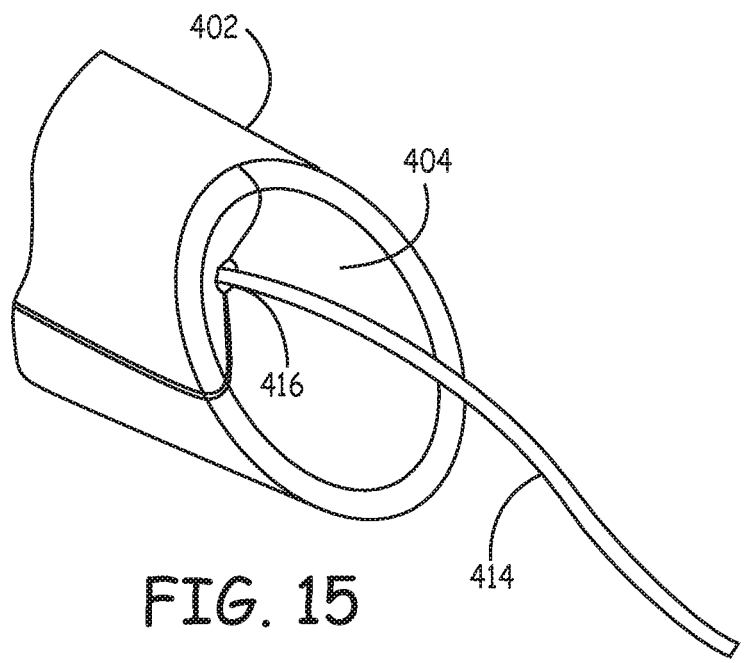
FIG. 15 is an exploded perspective view of the loading funnel of the actuation tool of FIG. 12.

Referring to FIG. 9, an actuation tool 200 comprises a support structure 202, a corewire connection 204 and an overtube connection 206 each connected to opposite ends of the support structure 202, a dial 208, and a button lock 210. Corewire connection 204 and overtube connection 206 interface with support structure 202 along a channel 220 that provides for passage of the corewire, as shown in FIG. 11. Corewire connection 204 and overtube connection 206 are gripping devices that respectively grip the corewire and overtube when engaged to provide for their relative longitudinal movement through rotation of dial 208.

Figure 10:
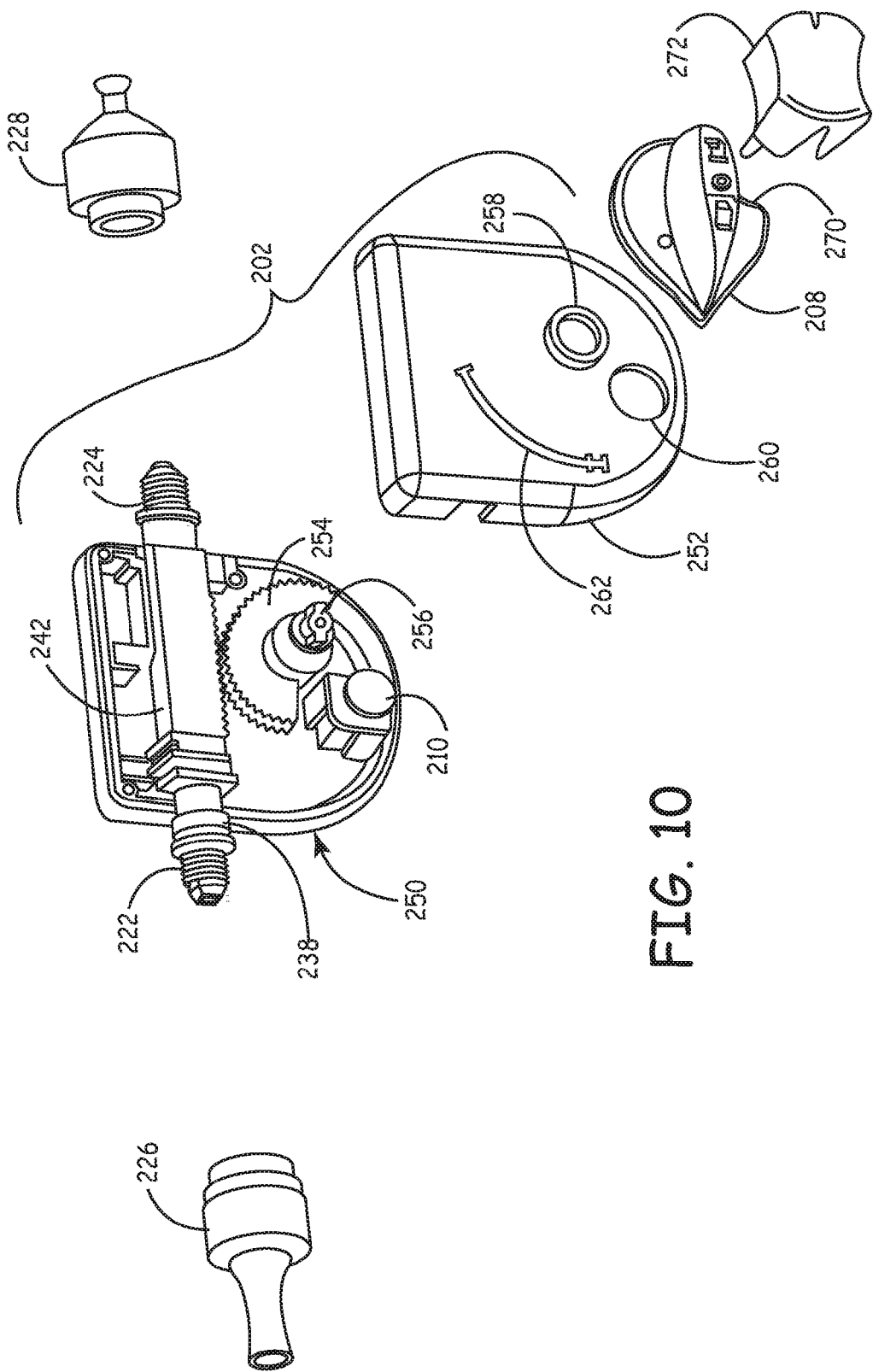
FIG. 10 is a perspective view of the actuation tool of FIG. 9 in a partially exploded format to show components internal to a housing.

Referring to FIGS. 9-11, in this embodiment, corewire connection 204 and overtube connection 206 are collets that comprise, respectively, threaded receiving sleeves 222, 224 and mated threaded caps 226, 228. Receiving sleeves have a taper and one or more slits such that channels through the receiving sleeves shrink in diameter when the mated cap is tightened such that the respective collets grip the overtube or corewire upon tightening. As shown in FIG. 11, sleeve 222 is integral with arm 238 that is securely attached to support structure 202, as shown in FIG. 9. Cap 226 can comprise a window 240, as shown in FIG. 9, for observing the corewire, such that it can be quickly determined if the corewire is properly loaded in the actuation tool. Referring to FIG. 11, corewire tubular channel 241 is connected to sleeve 222 to form a continuous corewire path into cap 226. Sleeve 224 is connected to sliding arm 242. Sliding arm 242 has an overtube channel 244, an overtube stop 246 that provided a limit on the insertion of the overtube with a corewire tubular channel 248 connected to sliding arm 242 extending beyond the overtube stop. Corewire tubular channel 248 has an inner diameter slightly larger than the outer diameter of corewire tubular channel 241 so that corewire tubular channel 248 slides over corewire tubular channel 241 when sliding arm 242 moves such that the corewire is supported essentially along its entire length within actuation tool 200.

While the embodiment shown in FIGS. 9-11 is based on collets, corewire connection 204 and overtube connection 206 can be based on other designs. For example, connections 204, 206 can comprise clamps that snap between locked and unlocked configurations, in contrast with the collets that screw into position. In some embodiments, a lever arm can be used to transition the connections between locked and unlocked positions. Various clamps designs in the art can be adapted as substitutes for the collets based on the disclosure herein.

Referring to an exploded view in FIG. 10 and a cut away exposed view in FIG. 11, the components internal to the support structure 202 comprises a control element that moves the corewire connection and the tube connection away from and toward each other to move the corewire and tube away from and toward each other, respectively. Referring to FIG. 10, support structure 202 comprises housing 250 and cover 252 that attached to housing 250 to cover the moving parts within housing 250. The control element can include a transmission comprising gear 254 that interfaces with sliding arm 242 such that rotation of gear 254 is converted to translation motion of sliding arm 242 such that the position of corewire connection 204 and overtube connection 206 can be adjusted. In particular, gear 254 and sliding arm 242 comprise teeth that cooperate with each other. Gear 254 is operably connected to a knob 256 that connects with dial 208. When dial 208 is rotated, gear 254 rotates with the dial 208 and the gear's teeth cooperate and move with the teeth of sliding arm 242 to convert the rotational movement of the dial 208 and gear 254 to translational movement of sliding arm 242 to move corewire connection 204 relative to overtube connection 206. Other transmission designs for converting rotational motion of the rotatable element to a translational motion of the corewire connection or the overtube connection can replace the design shown in FIG. 11 if desired.

Cover 252 comprises a first hole 258 for the passage of a portion of knob 256 to provide for connection to dial 208 and a second hole 260 for the passage of depressible button lock 210. Cover 252 can further comprise markings 262 to provide instructions. Dial 208 comprises a notch 270 that engages with button lock 210 at a particular rotation of dial 208 to prevent rotation of the dial 208 unless the button lock 210 is depressed. Button lock 210 can be constructed with a spring, such as a conventional spring structure or the like, or with other elastic material or appropriate construction. In some embodiments, notch 270 is positioned to engage button lock 210 at a dial position corresponding with the deployed configuration of the fiber cartridge corresponding with a particular relative position of the corewire and overtube. As shown in FIG. 9, actuation tool 200 can be supplied with a removable shipping lock 272 that interfaces with dial 208 and cover 252 to supply the dial at a particular orientation. Shipping lock 272 can be kept in position until the fiber-based device is placed within the patient and the operator is ready to deploy the fiber cartridge. Shipping lock 272 can be removed to deploy the fiber cartridge or other element within the patient. In alternative or additional embodiments, a second depressible button or the like can be used to hold dial 208 at a delivery position to resist premature deployment of the device. Furthermore, other appropriate locking features, such a frictional catch or the like, can replace the button lock to provide fixed positions of the dial at the deployed and/or delivery positions of the dial.

Referring to FIG. 11, a cut away exposed view of actuation tool 200 reveals the components internal to sliding arm 242 and arm 238. Arm 238 has a projecting sleeve 274 that extends within sliding arm 242 to facilitate the sliding motion of sliding arm 242 while keeping the channel aligned for the corewire. The clearance between the adjustable corewire tubular channel 248 and the corewire can be less than or equal to about 0.003 inch. Adjustable corewire tubular channel 248 can provide appropriate support for the entire length of the corewire exposed from the overtube through the locked position within the corewire connection 204. In some embodiments, adjustable corewire tubular channel 248 extends to leave less than about 0.001 inch of the corewire unsupported between the position at which the corewire exits the overtube and the locked position in corewire connection 204.

In operation, actuation tool 200 is constructed to actuate or de-actuate the fiber cartridge by taking an advantage of the configuration of the integrated guiding structure with the proximal end of the corewire extending from the proximal end of the tube. The proximal end of the corewire is inserted through overtube connection 206 and adjustable corewire tubular channel 248 into the corewire connection 204. The overtube contacts stop 246 to indicate full insertion of the overtube into overtube connection 206. The user can observe the corewire within observation window 240 to confirm that the corewire is properly positioned within the corewire connection 204. After the corewire is properly positioned corewire connection can be locked onto the corewire, and overtube connection can be similarly locked onto the overtube either before or after locking the corewire connection. Shipping lock 272 can be removed to rotate dial 208 to deploy the fiber cartridge or other device, and dial 208 is rotated until button lock 210 extends outward to engage notch 270 to lock the device in the deployed configuration. When dial 208 is rotated clockwise, gear 254 also rotates clockwise and causes translational movement of sliding arm 242 away from corewire connection 204, which increases the length of adjustable corewire tubular channel 248 which brings the tubes of the fiber cartridge toward each other to flare the fibers. When dial 208 is rotated counterclockwise upon depressing button lock 210, gear 254 also rotates counterclockwise and causes translational movement of sliding arm 242 toward corewire connection 204, which decreases the length of adjustable corewire tubular channel 248 to transition the fiber cartridge to a lower profile recovery configuration. The actuation tool can be temporarily removed for the loading of other instruments over the integrated guide structure.

An alternative embodiment of an actuation tool is shown in FIGS. 12-15. This tool is designed to grip the overtube and corewire simultaneously with two gripping elements, respectively. Referring to FIGS. 12-15, actuation tool 400 comprises a housing 402, a wire entry port 404, loading window 406, a wire release element 408 and an actuation dial 410. Housing 402 has an ergonomic design to facilitate use. Wire entry port 404 has a funnel shape to facilitate insertion of an integrated guide structure 414 into the opening 416. The internal channel for the overtube and core wire can be essentially as described above for FIGS. 9-11 within housing 402. Thus, the corewire is appropriately supported, and the corewire can be moved relative to the overtube for actuation purposes. Window 406 is formed from a transparent material, such as a plastic or glass material. This tip of the corewire 418 can be observed in window 406 to confirm proper loading of the corewire within the tool.

Wire release element 408 comprises a button that is depressed to unlock internal gripping elements to provide for insertion of the overtube and corewire into the guide channel within housing 402. The depression and release of release element 408 can be controlled with one or more suitable springs or the like. The release element may be a button. To control the opening of the internal gripping elements, depression of release element 408 can shift a moveable section of a wall along the guide channel to provide a suitable opening for the overtube of one gripping element and for the corewire at the other gripping element. Upon release of the button, the moveable section of the gripping element translates to grip the respective overtube or corewire. In alternative embodiments, release element 408 can be replaced with a lever or other moveable element that can be translated to lock and unlock the gripping elements.

Actuation dial 410 can function similarly to dial 208 in FIG. 9. Referring to FIGS. 12-14, dial 410 can be locked unless the central button 420 is depressed. In alternative embodiments, housing 402 can comprise buttons at adjacent positions to the dial to unlock the dial from the actuated or un-actuated positions. Similarly, dial 410 can comprise an alignment feature 422 for visualization of the status of the tool in which the housing has corresponding alignment features 424, 426, 428 to indicate correct positioning for actuation and un-actuating the device controlled with the guide structure inserted into the tool.

Figure 16:
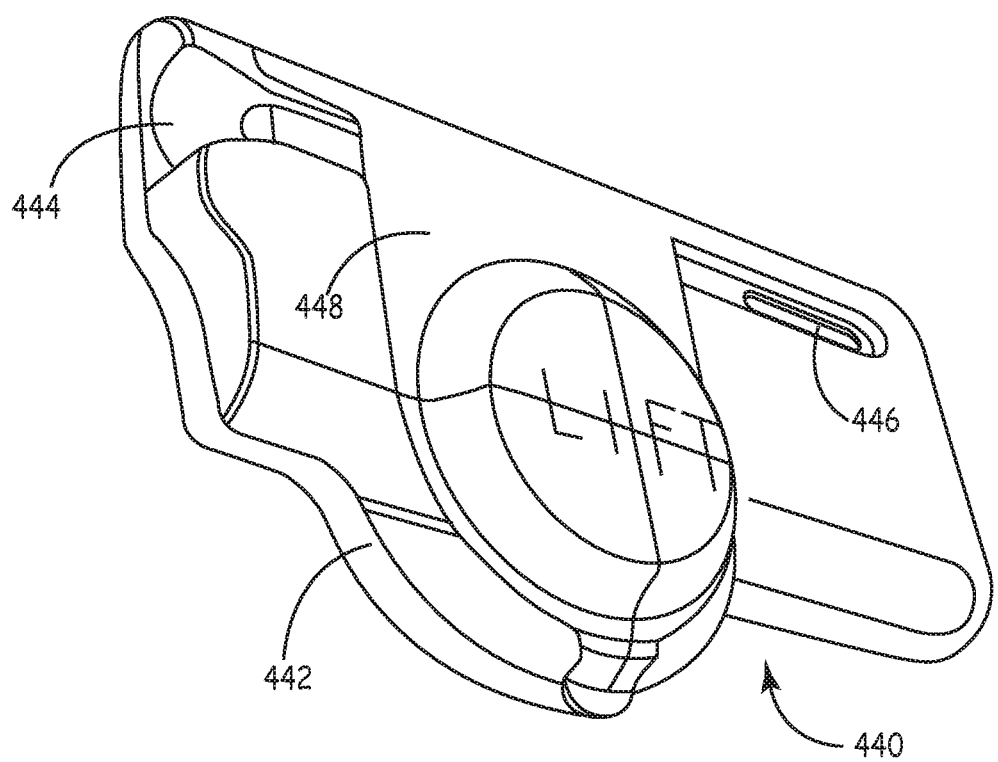
FIG. 16 is a top perspective view of a second alternative embodiment of an actuation tool in a load configuration.
Figure 17:
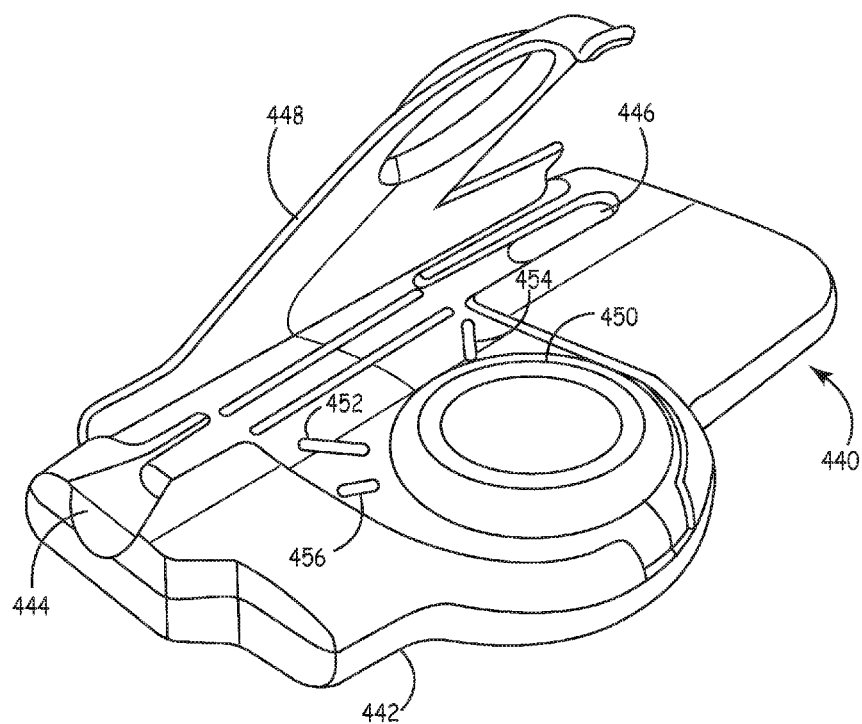
FIG. 17 is top perspective view of the actuation tool of FIG. 16 in an actuation configuration in which the dial is exposed.

Another alternative embodiment for the actuation tool is shown in FIGS. 16 and 17. The embodiment of FIGS. 16 and 17 is similar to the embodiment in FIGS. 12-15 except for the function of the locking and unlocking the gripping element. Referring to FIGS. 16 and 17, actuation tool 440 comprises a housing 442, a loading funnel 444, a viewing window 446, a lift cover 448, and an actuation dial 450. Lift cover 448 replaces release element 408 in the embodiment of FIGS. 12-15. Referring to FIGS. 16 and 17, lift cover 448 has a closed position in which cover 448 is enclosed. When lift cover 448 is closed, then gripping elements are open so that the integrated guide structure can be inserted through loading funnel 444 into housing 442. Referring to FIG. 17, cover 448 opens to an actuation position where the cover snaps into position to expose dial 450. Placement of cover 448 in the actuation position locks the overtube and corewire in position within housing 442. Then, with access available, dial 450 can be rotated between an initial position 452 and a deployed/actuated position 454 and then from an actuated position 454 to an un-actuated position 456. Un-actuated position 456 can be the same position or a different position from initial position 452. In particular, it can be desirable to have the unactuated position to extend beyond the initial position, as shown in FIG. 17, to place additional tension on the fiber bundle to place the device in a desired configuration for removal from the patient. Thus, to load a tool such as an aspiration catheter or a stent delivery catheter over the integrated guide structure, cover 448 can be placed in the closed position to release the integrated guide structure, which is then disconnected from the actuation tool for loading of the catheter and then replaced into the actuation tool. While the integrated guide structure is disconnected from the actuation tool, the dial cannot be accidentally rotated since it is covered.

Aspiration Catheter

The aspiration catheters described herein can be effectively used along with fiber-based devices, such as those described herein, or in separate procedures within a patient. The aspiration catheters generally have a rapid exchange construction, such as a single lumen rapid exchange design. The catheter can comprise a polymer material that is reinforced with metal wire or the like to balance mechanical strength and flexibility. Radiopaque marker bands can assist with visualization when the catheter is within a patient. It has been discovered that covering the radiopaque marker bands with the reinforcing metal wire prior to embedding the metal wire into the polymer can significantly decrease the chance of catching the marker bands on structure within the patient. If the marker bands catch on structure within the patient, such as a stent or anatomical structure, it can make it difficult to remove the aspiration catheter, the vessel within the patient can be damaged, and/or the marker bands can be disengaged from the catheter within the patient. In some embodiments, a narrow diameter extension can extend from the distal end of catheter to provide access into smaller vessels, such as blood vessel in the brain, such that the catheter can reach more locations while still providing desirable amounts of suction.

Referring to FIGS. 18 and 19, in a particular embodiment aspiration catheter 300 comprises a hollow tube 302, a rapid exchange segment 304 with a bent tip 306 and with a distal aspiration port 308 and a fitting 310 for attachment to a suction device, which is shown as a female Luer fitting. In some embodiments, a single lumen extends from fitting 310 through tube 302, through rapid exchange segment 304 to distal aspiration port 308. While it can be desirable for tube 302 to have a single lumen, in alternative embodiments tube 302 can have a plurality of lumen, such as two, three or more lumen, in which the lumen may or may not have different functions in the device. Fitting 310 comprises a handle 312 and a connection port 314.

A guidewire port 320 is located at the position at which rapid exchange segment 304 joins tube 302, as shown in FIGS. 18 and 18A. Rapid exchange segment 304 may or may not have a larger average diameter than tube 302. As shown in FIGS. 18A, 19 and 19A, the rapid exchange segment 304 has a larger diameter than the adjacent tube 302. The use of a larger diameter rapid exchange segment provides for easier entry of a fiber cartridge into the aspiration catheter for removal from the patient with less disruption of flow along the length of the catheter when the catheter is delivered into smaller blood vessels.

To facilitate observation of the catheter by x-ray when the catheter is within a body, one or more radiopaque bands can be positioned on the tube. Furthermore, visual marker bands can be placed near the proximal end of the aspiration catheter for evaluating the position along the fiber-based device for the portion of the devices outside from the patient. FIGS. 18, and 19 show a first radiopaque band 322 positioned at the distal tip of the catheter, and a second radiopaque band 324 positioned at a selected position on rapid exchange segment 304. Visual marker bands 326, 328 are also shown in the embodiment of FIGS. 18 and 19.

The catheter can have sufficiently small diameters for entry into small arteries of the brain or other small vessels. In particular, in some embodiments, the rapid exchange segment or a portion thereof can have a smaller diameter than the average diameter of the tube. Referring to FIG. 20, aspiration catheter 350 for accessing smaller vessels comprises a tube 352, a rapid exchange segment 354, a rapid exchange port 356 at the position at which rapid exchange segment joins tube 352 and a reduced diameter distal segment 358 with an average diameter smaller relative to the average diameter of the tube with a curved distal tip 360 having a radiopaque marker band 362. While the proximal end of catheter 350 is not shown in FIG. 20, catheter 350 can have fittings similar to those shown in FIGS. 18 and 19 or other suitable fittings. While FIG. 20 shows distal segment 358 including only a portion of rapid exchange segment 354, in other embodiments a rapid exchange port is located adjacent the distal segment such that the rapid exchange segment is the same as the distal segment.

Distal segment 358 can have an outer diameter from about 25 percent to about 95 percent of the average outer diameter of the tube of the catheter, and in further embodiments from about 45 to about 90 percent and in additional embodiments from about 60 to about 85 percent of the average diameter of the tube. For example, the distal tip can have an outer diameter range from about 0.015 to about 0.120 inches, and the tube can have an outer diameter range from about 0.030 to about 0.150 inches, in other embodiments from about 0.040 to about 0.125 inches and in further embodiments from about 0.045 to about 0.120 inches. A person of ordinary skill in the art will recognize that additional ranges of dimensions within the explicit ranges above are contemplated and are within the present disclosure.

As shown in FIGS. 18, 19 and 20, the distal tip can also be bent or curved to provide improved tracking during delivery into a patient's vessel by controlling tracking along a guide structure extending from the tip. The curved tip facilitates tracking of the catheter along the guide structure with a reduced tendency of the catheter to redirect the guide structure at branches or curves in the vessel. The guide structure deflects the bent tip such that the guide structure at least partially guards the opening of the aspiration catheter during the delivery of the guide catheter through the patient's vessel. The curved tip deflects the sharp edge of the tip away from the vessel wall and naturally tracks along the guide structure with little drifting since the curve creates a tight transition from the wire to the catheter on one side of the curve. The tip opening presents a small profile for snagging and tracks closely along the path of the guide structure as it is pushed along the guide structure. Optionally, the tip is provided with a beveled edge.

The angle of the curved tip relative to a straight tip generally is less than 90 degrees and can be, for example, from about 10 degrees to about 60 degrees. The selected angle corresponds with a radius of curvature. In some embodiments, the straight portion of the tip after the curve can have a length less than about 1 cm, and in other embodiments from about 0.1 mm to about 6 mm and in further embodiments from about 0.5 mm to about 4 mm. In other embodiments, the curve consists of a gradual arc with no straight section distal to it. A person of ordinary skill in the art will recognize that additional ranges of angles and lengths within the explicit ranges above are contemplated and are within the present disclosure.

The curved tip can be formed using any suitable approach, such as molding the curved tip in the desired configuration or heating the material on a curved mandrel or in a curved trough to a softening temperature and then cooling the material on the mandrel/in the trough to fix the shape. The edge of curved tip at the opening of the catheter can be cut straight perpendicular to the axis of the tip at the opening or at an angle relative to a straight cut. Alternatively, the edge can have a non-planar contour. In alternative embodiments, the catheter tip is not curved. Aspiration catheter designs with improved tracking are also discussed in published U.S. application 2007/0060944 to Boldenow et al., entitled "Tracking Aspiration Catheter," incorporated herein by reference. A loading tool can be used to facilitate guiding a guidewire or integrated guiding structure from the distal aspiration opening through the guide port. A suitable loading tool can comprise a tube with a docking cavity that can accept the proximal end of the guide to feed it through the guide port.

Figure 21:
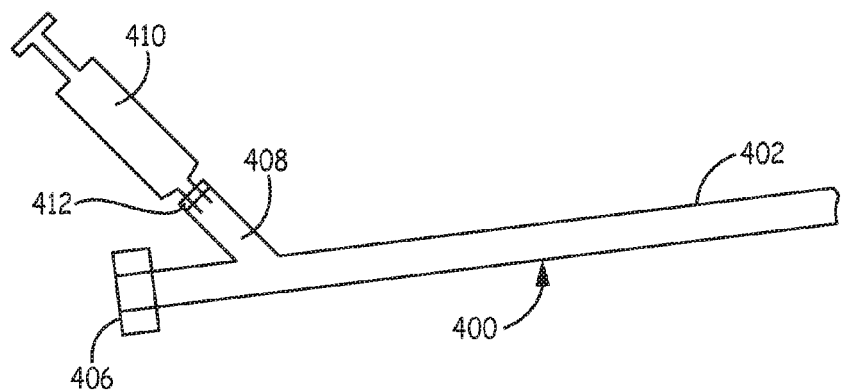
FIG. 21 is a fragmentary side view of the proximal section of an aspiration catheter with an over the wire design.

Referring to FIG. 21, aspiration catheter 400 comprises apart from the distal end a shaft 402, a proximal end 406, an aspiration connection 408, and a suction device 410. In some embodiments, an aspiration connection 408 can provide for connection of a suction device 410 with a lumen extending through shaft 402. Aspiration connection 408 can be placed at the proximal end or other location near the proximal end, as convenient. Generally, aspiration connection 408 comprises a fitting 412 or the like to provide a sealed connection with the suction device 410. In other embodiments the suction device can be formed as an integral part of the proximal end 406 such that no fitting or other connection is used. Suitable suction devices include, a suction device that can deliver a selected amount of suction, such as a syringe, a compressed bladder, a pump, such as a peristaltic pump or a piston pump, or the like. A tube or the like can be used to connect the suction device 410 to aspiration connection 412.

Aspiration catheters can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates or other suitable biocompatible polymers. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. Generally, different sections of aspiration catheter can be formed from different materials from other sections, and sections of aspiration catheter can comprise a plurality of materials at different locations and/or at a particular location. In particular, it may be desirable to form distal compartment or a portion thereof from an elastomeric polymer, such as suitable polyurethanes, polydimethyl siloxane and polytetrafluoroethylene. In addition, selected sections of the catheter can be formed with materials to introduce desired stiffness/flexibility for the particular section of the catheter. Similarly, fitting can be formed form a suitable material, such as one or more metals and/or one or more polymers.

In embodiments of particular interest, the catheter or appropriate portion thereof comprises a thermoplastic polymer with embedded metal wire, which reinforces the polymer. Suitable polymers include, for example, polyamides, i.e., nylons. The wire can be braided, coiled or otherwise placed over a polymer tubing liner with some tension to keep the wire in place over the tubing liner. A polymer jacket is then placed over the top. Upon heating to a temperature over the softening temperature of the polymer and subsequent cooling, the wire becomes embedded within the polymer. The liner and jacket can be the same or different materials. Suitable wire includes, for example, flat stainless steel wire. The wire adds additional mechanical strength while maintaining appropriate amounts of flexibility. The wire can provide some radio-opacity although radiopaque bands generally would provide a darker and distinguishable image relative to the wire. However, the image of the wire can provide further visualization of the catheter during the procedure.

To decrease the chance of accidental removal of the radiopaque band from the catheter and to decrease the chance of the radiopaque band catching onto other objects within the vessel, a metal reinforcing wire can be used to cover or enclose the radiopaque band with the metal wire subsequently being embedded within the polymer. As described in the previous paragraph, the metal wire can comprise interwoven wires, coil, or the like. A polymer jacket is placed over the metal wire, which is correspondingly covering the radiopaque band(s). Heat bonding then forms the resulting reinforced catheter. It has been found advantageous to have the braid-wire extend over the outer surface of the radiopaque band. This prevents the band from being separated from the catheter in the event that the wall is kinked or collapsed. If collapse or kinking of the catheter wall occurs, the braid-wire over the surface of the band collapses down over the marker band to prevent it from separating from the structure.

Use of Aspiration Catheter with Filtration Device

In general, the aspiration catheters described herein can be used for a variety of procedures. For example, aspiration catheters are particularly useful for the removal of a fiber-based device from the vessel of a patient. In particular, aspiration can be effective to capture any emboli that may be released while the fiber cartridge is being converted from a deployed configuration to an appropriate configuration for removal. The single lumen design of the rapid exchange catheter provides for improved loading of the fiber cartridge into the catheter while providing improved aspiration function. The fiber cartridge can be used as an embolism protection device in which the fiber cartridge is placed into a stationary position to capture emboli generated during other treatment procedures within the vessel such as an angioplasty procedure, stent delivery or the like. In other embodiments, the fiber-based and catheter can be used in an embolectomy procedure in which an emboli blocking flow in the vessel are pulled with the fiber cartridge to the aspiration catheter for removal of the emboli. Furthermore, the aspiration catheter can be used in a thrombectomy procedure in which the aspiration catheter is used without a filter or the like to aspirate thrombus deposits from within the vessel.

To stabilize the recovery process for a fiber-based device, the fiber cartridge can be drawn into the distal end of the aspiration catheter. Once the fiber cartridge is comfortably within the distal compartment of the aspiration catheter, the risk of release of emboli is sufficiently reduced that the suction can be stopped and the fiber-based device safely withdrawn with the catheter from the vessel of the patient. Thus, by drawing the fiber cartridge into a distal segment of the catheter, the disruption of natural flow in the vessel due to the suction can be kept to a level such that a shunt for the flow generally is not used.

In general, the appropriate amount of time to apply aspiration depends on the specific procedure with an increased amount of time favoring additional collection of clots or debris while longer times for aspiration can lead to a longer period of the disruption of nature flow in the vessel. Using the improved fiber based devices described herein and in copending applications cited herein, procedures can be safely performed without blocking the flow through the patient's vessel. Similarly, the use of a fiber-based device with a three dimensional filtration matrix provides for removal of the device into the aspiration catheter without blocking suction into the catheter through flow through the matrix and/or by having a recovery configuration for the fiber cartridge that does not block flow. Depending on the vessel, the amount of disruption of the flow that can be safely tolerated can be estimated, such that the process for the recovery of the embolism protection device can be accordingly determined. To keep disruption of the flow to lesser levels, the suction generally is applied starting shortly before the recovery process begins. Suction generally can be maintained during the constriction of the device configuration for fitting within the distal compartment and while the device is drawn within the distal compartment. The suction generally is stopped once the device is within the distal compartment and the device is not moved relative to the aspiration catheter. Once the device is safely within the distal compartment, the aspiration catheter can be removed from the patient along with the fiber-based device.

To draw the fiber cartridge within the distal compartment of the aspiration catheter, the fiber cartridge can be converted from a deployed configuration across the vessel lumen to a recovery configuration, generally with a reduced area across the cross section of the vessel lumen, in which the device fits within the distal compartment of the catheter. The recovery configuration generally is similar to the delivery configuration.

The overall timing of the recovery process involves a balance between several factors within the overall objective of keeping the period of application of suction within desired ranges. To meet the objectives, it is desirable to transform the fiber cartridge to the recovery configuration and load the fiber cartridge into the distal end of the aspiration catheter relatively quickly. However, sharp impacts or abrupt motions of the device raise the possibility of releasing emboli. Therefore, the loading of the device can be performed as quickly as possible with a smooth motion. In general, it is desirable for the total time to transform the device to the recovery configuration and to load the device within the distal compartment to be no more than about five minutes, in other embodiments, no more than about 3 minutes, in additional embodiments from about 2 seconds to about 2 minutes and in further embodiments from about 5 seconds to about 1.5 minutes.

The suction is contrary to the flow within the vessel with is otherwise relatively unrestricted. The suction rate can be greater than the flow within the vessel or some fraction of the flow. Specifically, the suction rate can be no more than about 125 percent of the vessel flow, in further embodiments, no more than about 110 percent of the vessel flow, in further embodiments from about 25 percent to about 100 percent and in additional embodiments from about 50 percent to about 80 percent of the unrestricted flow through the vessel. As a particular example, if the unrestricted flow through the aorta is 5 liters per minute, the suction rate can be 125 percent of the flow or 6.25 liters per minute or the suction rate can be 25 percent of the flow or 1.25 liters per minute. A person of ordinary skill in the art will recognize that additional ranges of flow rates and flow percentages are contemplated and are within the present disclosure. If the suction rate is greater than the natural flow rate, the suction tends to draw fluid from both sides of the fiber cartridge into the aspiration catheter. If the suction rate is less than the natural flow rate, the suction tends to draw fluid from the portion of the vessel adjacent the opening of the aspiration catheter. The suction rate can be selected to balance the disruption of the flow with the collection rate for any released emboli. In some embodiments, the flow rate can change at different points in the recovery process. For variable suction rate embodiments, the suction rate is generally greater at the start of the recovery process and reduced once the device is collapsed to a recovery configuration.

Aspiration catheters are discussed in detail in application Ser. No. 10/854,920, now U.S. Pat. No. 8,409,237 to Galdonik et al. entitled "Emboli Filter Export System," filed May 27, 2004 and application Ser. No. 11/207,169, now U.S. Pat. No. 8,021,351 to Galdonik et al. entitled "Tracking Aspiration Catheter," filed Aug. 18, 2005.

Distribution and Packaging

The medical devices described herein are generally packaged in sterile containers for distribution to medical professionals for use. The articles can be sterilized using various approaches, such as electron beam irradiation, gamma irradiation, ultraviolet irradiation, chemical sterilization, and/or the use of sterile manufacturing and packaging procedures. The articles can be labeled, for example with an appropriate date through which the article is expected to remain in fully functional condition. The components can be packaged individually or together.

Various devices described herein can be packaged together in a kit for convenience. The kit can further include, for example, labeling with instruction for use and/or warnings, such as information specified for inclusion by the Food and Drug administration. Such labeling can be on the outside of the package and/or on separate paper within the package.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. An aspiration catheter comprising:
an aspiration device,
a proximal portion,
a connection port connected to the proximal portion, wherein the connection port is connected to the aspiration device,
a distal segment wherein the distal segment comprises a single lumen and wherein the distal segment comprises one or more polymers including at least one thermoplastic polymer forming a tubular element and metal wire reinforcement embedded in the polymer tubular element and extending around the tubular element, and
a tube section connected between the distal segment and the proximal portion,
wherein the distal segment has a constant outer diameter with a value that is from about 25 percent to about 95 percent of the average outer diameter of the tube section and comprises a distal opening at the distal end of the catheter,
wherein the catheter comprises a continuous lumen extending from the proximal portion through the tube section and the distal segment to the distal opening that provides fluid communication between the aspiration device and the distal opening, and the portion of the continuous lumen inside the distal segment has a smaller diameter relative to the diameter of the portion of the continuous lumen inside the tube section, wherein the diameter of the distal segment is not extendible.

2. The aspiration catheter of claim 1 wherein the constant diameter of the distal segment is from about 45 percent to about 85 percent of the average outer diameter of the tube section.

3. The aspiration catheter of claim 1 wherein the constant diameter of the distal segment is from about 0.015 inches to about 0.120 inches.

4. The aspiration catheter of claim 1 wherein the constant diameter of the distal segment is no more than 0.040 inches.

5. The aspiration catheter of claim 1 wherein the polymer comprise polyamides or nylons, polyurethanes, polydimethyl siloxane, or polytetrafluoroethylene and wherein the distal segment further comprises one or more radiopaque markers.

6. The aspiration catheter of claim 1 wherein the metal wire comprises Nitinol or stainless steel.

7. The aspiration catheter of claim 1 further comprising radiopaque marker on the distal segment of the catheter.

8. The aspiration catheter of claim 1 further comprising exterior visual marker on the proximal portion of the catheter.

9. The aspiration catheter of claim 1 wherein the connection port is connected to a syringe.

10. A method of using the catheter of claim 1 in a thrombectomy procedure, the method comprising,
tracking the aspiration catheter along a guide structure to place the distal segment into a small blood vessel with the distal opening of the catheter close to thrombus deposits within the vessel, and
applying suction through the proximal portion to effect aspiration at the distal opening of the catheter to aspirate the thrombus deposits from the vessel,
wherein the small blood vessel is an artery of the brain.

11. The method of claim 10 wherein the suction rate is no more than about 125 percent of the vessel flow.

12. The aspiration catheter of claim 1 further comprising wherein the distal portion of the distal segment is a curved distal tip.

13. The aspiration catheter of claim 12 wherein the angle of the curved tip relative to a straight tip is from about 10 degrees to about 60 degrees.

14. The aspiration catheter of claim 12 further comprising a guide structure deflecting the curved distal tip.

15. The aspiration catheter of claim 1 wherein the tip of the distal end of the catheter is beveled.

16. The aspiration catheter of claim 1 wherein the length of the distal segment is at least 1.0 centimeters.

17. The aspiration catheter of claim 1 wherein the distal portion segment comprises a rapid exchange segment.

* * * * *